(12) United States Patent
Cho

(10) Patent No.: US 9,986,957 B2
(45) Date of Patent: Jun. 5, 2018

(54) RADIATION DETECTOR AND COMPUTED TOMOGRAPHY APPARATUS USING THE SAME

(71) Applicant: SAMSUNG ELECTRONICS CO., LTD., Suwon-si (KR)

(72) Inventor: Min-kook Cho, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 160 days.

(21) Appl. No.: 14/539,202

(22) Filed: Nov. 12, 2014

(65) Prior Publication Data

US 2015/0131776 A1    May 14, 2015

(30) Foreign Application Priority Data

Nov. 12, 2013 (KR) .................. 10-2013-0137118
Nov. 5, 2014  (KR) .................. 10-2014-0152859

(51) Int. Cl.
| | | |
|---|---|---|
| *A61B 6/03* | (2006.01) | |
| *G01T 1/24* | (2006.01) | |
| *A61B 6/00* | (2006.01) | |
| *G01N 23/02* | (2006.01) | |
| *G01N 23/04* | (2018.01) | |

(52) U.S. Cl.
CPC ............ *A61B 6/4241* (2013.01); *A61B 6/032* (2013.01); *A61B 6/4233* (2013.01); *A61B 6/482* (2013.01); *G01N 23/02* (2013.01); *G01N 23/046* (2013.01); *G01T 1/24* (2013.01); *G01T 1/247* (2013.01)

(58) Field of Classification Search
CPC ..... A61B 6/032; A61B 6/4233; A61B 6/4241; A61B 6/482; G01T 1/24

USPC .................. 378/5, 19, 98.8; 250/370.09
See application file for complete search history.

(56) References Cited

U.S. PATENT DOCUMENTS

| | | | | |
|---|---|---|---|---|
| 5,943,388 | A * | 8/1999 | Turner ............... | G01V 5/0041 378/98.11 |
| 6,034,373 | A * | 3/2000 | Shahar ............. | H01L 27/14676 250/338.4 |
| 6,175,611 | B1 * | 1/2001 | Melen ............... | G01T 1/243 250/332 |
| 6,246,747 | B1 * | 6/2001 | Wear ................ | G01N 23/083 378/98.11 |
| 6,255,654 | B1 * | 7/2001 | Verbinski ........... | G01V 5/0016 250/358.1 |

(Continued)

FOREIGN PATENT DOCUMENTS

| | | |
|---|---|---|
| JP | 2011-117969 A | 6/2011 |
| JP | 2013-40935 A | 2/2013 |

(Continued)

OTHER PUBLICATIONS

International Search Report for PCT/KR2014/010876 dated Feb. 24, 2015 [PCT/ISA/220 & 210].

(Continued)

*Primary Examiner* — Allen C. Ho
(74) *Attorney, Agent, or Firm* — Sughrue Mion, PLLC

(57) ABSTRACT

The radiation detector includes image pixels that each includes a counting pixel, to restore an image. The counting pixel includes a radiation absorption layer, which converts incident photons into an electrical signal, and a photon processor that counts a number of the photons, based on the electrical signal.

16 Claims, 13 Drawing Sheets

(56) References Cited

U.S. PATENT DOCUMENTS

| | | | |
|---|---|---|---|
| 6,408,050 B1 * | 6/2002 | Han | G01T 1/17 378/98.11 |
| 6,720,812 B2 * | 4/2004 | Turner | H04N 5/335 327/170 |
| 6,927,396 B2 * | 8/2005 | Vydrin | G01T 1/1644 250/366 |
| 6,928,144 B2 * | 8/2005 | Li | A61B 6/032 250/370.09 |
| 7,068,750 B2 * | 6/2006 | Toth | A61B 6/032 378/156 |
| 7,068,751 B2 * | 6/2006 | Toth | A61B 6/032 378/20 |
| 7,138,635 B2 * | 11/2006 | Heismann | G01T 1/1611 250/370.09 |
| 7,139,362 B2 * | 11/2006 | Heismann | A61B 6/032 378/5 |
| 7,145,986 B2 * | 12/2006 | Wear | G01T 1/366 250/370.09 |
| 7,193,217 B2 * | 3/2007 | Heismann | G01T 1/2928 250/370.09 |
| 7,260,174 B2 * | 8/2007 | Hoffman | A61B 6/032 250/363.09 |
| 7,263,167 B2 * | 8/2007 | Walter | A61B 6/032 378/116 |
| 7,313,217 B2 * | 12/2007 | Toth | A61B 6/032 378/20 |
| 7,332,724 B2 * | 2/2008 | Hefetz | A61B 6/032 250/370.06 |
| 7,369,642 B2 * | 5/2008 | Eilbert | G01N 23/04 378/57 |
| 7,403,589 B1 * | 7/2008 | Short | A61B 6/032 250/370.11 |
| 7,473,902 B2 | 1/2009 | Spahn | |
| 7,479,639 B1 * | 1/2009 | Shahar | G01T 1/17 250/370.06 |
| 7,480,362 B2 * | 1/2009 | Carmi | A61B 6/032 378/19 |
| 7,486,764 B2 * | 2/2009 | Tkaczyk | G01T 1/249 250/370.09 |
| 7,488,945 B2 * | 2/2009 | Li | G01T 1/2928 250/370.09 |
| 7,518,116 B2 * | 4/2009 | Janssen | G03B 42/02 250/370.09 |
| 7,532,703 B2 * | 5/2009 | Du | A61B 6/032 378/116 |
| 7,573,040 B2 * | 8/2009 | Tkaczyk | G01T 1/242 250/370.09 |
| 7,583,779 B2 * | 9/2009 | Tkaczyk | A61B 6/032 378/4 |
| 7,592,596 B2 * | 9/2009 | Klein | G01T 1/171 250/361 R |
| 7,606,347 B2 * | 10/2009 | Tkaczyk | A61B 6/032 378/19 |
| 7,613,274 B2 * | 11/2009 | Tkaczyk | A61B 6/032 378/19 |
| 7,615,754 B2 * | 11/2009 | Liu | G01T 1/2018 250/370.09 |
| 7,634,061 B1 * | 12/2009 | Tümer | G01T 1/247 378/62 |
| 7,663,120 B2 | 2/2010 | Tomita et al. | |
| 7,668,289 B2 | 2/2010 | Proksa et al. | |
| 7,696,483 B2 * | 4/2010 | Tkaczyk | G01T 1/171 250/370.06 |
| 7,760,123 B2 * | 7/2010 | Rao | G06G 7/18 341/155 |
| 7,769,138 B2 * | 8/2010 | Dafni | A61B 6/4233 378/98.11 |
| 7,829,860 B2 * | 11/2010 | Nygard | G01T 1/2018 250/366 |
| 7,902,976 B2 * | 3/2011 | Doughty | G01T 1/026 250/370.1 |
| 7,916,836 B2 * | 3/2011 | Tkaczyk | G01T 1/24 250/370.09 |
| 8,000,434 B2 * | 8/2011 | Ziegler | G01T 1/2985 378/4 |
| 8,044,681 B2 * | 10/2011 | Rao | A61B 6/037 250/208.1 |
| 8,120,683 B1 * | 2/2012 | Turner | H01L 27/14634 250/370.09 |
| 8,159,286 B2 * | 4/2012 | Rao | G01T 1/2985 327/337 |
| 8,164,063 B2 * | 4/2012 | Frach | G01T 1/2985 250/363.04 |
| 8,198,577 B2 * | 6/2012 | Dierickx | G01T 1/17 250/214 DC |
| 8,213,566 B2 * | 7/2012 | Roessl | A61B 5/4869 378/5 |
| 8,373,135 B2 * | 2/2013 | Kappler | G01T 1/247 250/336.1 |
| 8,378,307 B2 * | 2/2013 | Baeumer | G01T 1/2985 250/362 |
| 8,389,928 B2 * | 3/2013 | Hackenschmied | G01T 1/249 250/252.1 |
| 8,440,957 B2 * | 5/2013 | Dierickx | G01T 1/17 250/214 R |
| 8,450,695 B2 * | 5/2013 | Kappler | G01T 1/17 250/370.09 |
| 8,581,200 B2 * | 11/2013 | Engel | G01T 1/2928 250/370.09 |
| 8,680,474 B2 * | 3/2014 | Soh | H01L 27/14609 250/370.09 |
| 8,729,485 B2 * | 5/2014 | Soh | H04N 5/32 250/370.09 |
| 8,772,730 B2 * | 7/2014 | Han | G01T 1/247 250/363.01 |
| 8,810,416 B2 | 8/2014 | Doughty et al. | |
| 8,891,845 B2 * | 11/2014 | Ogawa | A61B 6/14 382/128 |
| 8,927,937 B2 * | 1/2015 | Schwarzman | G01T 1/24 250/370.01 |
| 8,937,275 B2 * | 1/2015 | Kulik | 250/214 R |
| 8,941,076 B2 * | 1/2015 | Abraham | G01T 1/171 250/336.1 |
| 8,957,361 B2 * | 2/2015 | Han | A61B 6/4241 250/214 A |
| 8,958,531 B2 * | 2/2015 | Okamoto | G21K 1/062 378/145 |
| 8,971,496 B2 * | 3/2015 | Okamoto | G21K 1/06 378/145 |
| 8,988,267 B1 * | 3/2015 | Kimura | G01T 1/2928 341/155 |
| 9,000,385 B2 * | 4/2015 | Dror | G01T 1/171 250/370.06 |
| 9,014,455 B2 * | 4/2015 | Oh | A61B 6/52 378/98.11 |
| 9,031,197 B2 * | 5/2015 | Spahn | H04N 5/32 378/98.8 |
| 9,063,240 B2 * | 6/2015 | Herrmann | G01T 7/005 |
| 9,075,147 B2 * | 7/2015 | Schroter | G01T 1/247 |
| 9,100,601 B2 * | 8/2015 | Nishihara | H04N 5/378 |
| 9,113,839 B2 * | 8/2015 | Morton | A61B 6/032 |
| 9,128,195 B2 * | 9/2015 | Soh | H04N 5/32 |
| 9,149,241 B2 * | 10/2015 | Kim | A61B 6/482 |
| 9,160,939 B2 * | 10/2015 | Funaki | H03M 1/145 |
| 9,164,183 B2 * | 10/2015 | Kraft | G01T 1/40 |
| 9,176,238 B2 * | 11/2015 | Herrmann | G01T 1/17 |
| 9,207,332 B2 * | 12/2015 | Spahn | G01T 1/17 |
| 9,239,391 B2 * | 1/2016 | Han | G01T 1/17 |
| 9,254,113 B2 * | 2/2016 | Kim | A61B 6/4241 |
| 9,268,035 B2 * | 2/2016 | Herrmann | G01T 1/17 |
| 9,269,168 B2 * | 2/2016 | Inglese | A61B 6/4241 |
| 9,274,235 B2 * | 3/2016 | Kang | G01N 23/04 |
| 9,291,721 B2 * | 3/2016 | Han | G01T 1/247 |
| 9,291,724 B2 * | 3/2016 | Proksa | G01T 1/24 |
| 9,294,700 B2 * | 3/2016 | Nishihara | H01L 27/14603 |
| 9,301,378 B2 * | 3/2016 | Steadman Booker | G01T 1/24 |
| 9,310,490 B2 * | 4/2016 | Abraham | G01T 1/17 |
| 9,335,424 B2 * | 5/2016 | Herrmann | G01T 1/171 |

(56) References Cited

U.S. PATENT DOCUMENTS

| | | | |
|---|---|---|---|
| 9,344,661 B2* | 5/2016 | Saito | G01T 1/208 |
| 9,351,701 B2* | 5/2016 | Yamakawa | A61B 6/025 |
| 9,354,331 B2* | 5/2016 | Sagoh | A61B 6/032 |
| 9,389,320 B2* | 7/2016 | Ogawa | A61B 6/14 |
| 9,408,585 B2* | 8/2016 | Oh | A61B 6/484 |
| 9,411,055 B2* | 8/2016 | Yoon | G01T 1/247 |
| 9,416,022 B2* | 8/2016 | Saito | C01G 29/00 |
| 9,417,339 B2* | 8/2016 | Spahn | G01T 1/247 |
| 9,417,345 B2* | 8/2016 | Reitz | G01T 7/005 |
| 9,423,515 B2* | 8/2016 | Roessl | G01T 1/241 |
| 9,423,517 B2* | 8/2016 | Kang | G01T 7/005 |
| 9,444,344 B2* | 9/2016 | Kim | G01T 1/247 |
| 9,488,739 B2* | 11/2016 | Pelc | G01T 1/247 |
| 9,492,132 B2* | 11/2016 | Oh | A61B 6/482 |
| 9,504,438 B2* | 11/2016 | Proksa | G01T 1/24 |
| 9,504,439 B2* | 11/2016 | Yi | A61B 6/5205 |
| 9,517,045 B2* | 12/2016 | Kang | G01N 23/087 |
| 9,533,173 B2* | 1/2017 | Manzke | A61B 6/4241 |
| 9,535,167 B2* | 1/2017 | Proksa | G01T 1/171 |
| 9,535,172 B2* | 1/2017 | Lee | G01T 1/24 |
| 9,538,107 B2* | 1/2017 | Chappo | A61B 6/032 |
| 9,577,645 B2* | 2/2017 | Yoon | H03K 21/10 |
| 9,579,075 B2* | 2/2017 | Besson | G01T 1/2985 |
| 9,595,101 B2* | 3/2017 | Kato | G06T 11/005 |
| 9,599,730 B2* | 3/2017 | Spahn | G01T 1/247 |
| 9,602,745 B2* | 3/2017 | Nishihara | H04N 5/378 |
| 9,645,260 B2* | 5/2017 | Abraham | G01T 1/247 |
| 9,653,509 B2* | 5/2017 | Nishihara | H01L 27/14643 |
| 9,655,575 B2* | 5/2017 | Park | A61B 6/461 |
| 9,655,583 B2* | 5/2017 | Proksa | A61B 6/54 |
| 9,664,797 B2* | 5/2017 | Roessl | G01T 1/17 |
| 9,664,798 B2* | 5/2017 | Kappler | G01T 1/17 |
| 9,668,706 B2* | 6/2017 | Kim | A61B 6/563 |
| 9,675,309 B2* | 6/2017 | Kim | A61B 6/4266 |
| 9,678,220 B2* | 6/2017 | Herrmann | G01T 1/17 |
| 9,693,743 B2* | 7/2017 | Arakita | G01T 1/1606 |
| 9,700,268 B2* | 7/2017 | Kang | A61B 6/542 |
| 9,720,100 B2* | 8/2017 | Habib | H04N 5/2175 |
| 9,730,665 B2* | 8/2017 | Choi | A61B 6/5264 |
| 9,743,893 B2* | 8/2017 | Inglese | A61B 6/14 |
| 9,746,566 B2* | 8/2017 | Herrmann | G01T 1/247 |
| 9,750,471 B2* | 9/2017 | Schirra | A61B 6/4241 |
| 9,759,822 B2* | 9/2017 | Daerr | G01T 1/17 |
| 9,778,379 B2* | 10/2017 | Sagoh | G01T 1/208 |
| 9,784,854 B2* | 10/2017 | Blevis | G01T 1/2928 |
| 9,791,384 B2* | 10/2017 | Sung | G01N 23/04 |
| 9,854,656 B2* | 12/2017 | Goderer | H05G 1/58 |
| 9,867,590 B2* | 1/2018 | Tamura | A61B 6/585 |
| 2005/0285043 A1 | 12/2005 | Nascetti et al. | |
| 2006/0081785 A1 | 4/2006 | Heismann et al. | |
| 2007/0120062 A1 | 5/2007 | Li et al. | |
| 2008/0099689 A1 | 5/2008 | Nygard et al. | |
| 2008/0205585 A1 | 8/2008 | Proksa et al. | |
| 2009/0304149 A1 | 12/2009 | Herrmann et al. | |
| 2010/0111248 A1 | 5/2010 | Baeumer et al. | |
| 2010/0172466 A1 | 7/2010 | Herrmann et al. | |
| 2010/0282972 A1 | 11/2010 | Carmi et al. | |
| 2010/0301224 A1 | 12/2010 | Morel et al. | |
| 2013/0041628 A1 | 2/2013 | Han et al. | |
| 2013/0051648 A1 | 2/2013 | Kim et al. | |
| 2013/0105701 A1 | 5/2013 | Han et al. | |
| 2014/0284492 A1 | 9/2014 | Han et al. | |

FOREIGN PATENT DOCUMENTS

| | | |
|---|---|---|
| KR | 10-2005-0004179 A | 1/2005 |
| KR | 10-2008-0113012 A | 12/2008 |
| KR | 10-2009-0025926 A | 3/2009 |
| KR | 10-2013-0024225 A | 3/2013 |
| KR | 10-2013-0048001 A | 5/2013 |
| WO | 2004/071299 A1 | 8/2004 |
| WO | 2005/008286 A2 | 1/2005 |
| WO | 2006/117720 A2 | 11/2006 |
| WO | 2008/020379 A2 | 2/2008 |
| WO | 2008104911 A2 | 9/2008 |
| WO | 2009/017348 A2 | 2/2009 |

OTHER PUBLICATIONS

Written Opinion for PCT/KR2014/010876 dated Feb. 24, 2015 [PCT/ISA/237].

Communication from the European Patent Office dated May 8, 2015 in a counterpart European Application No. 14192619.6.

Communication dated Feb. 28, 2017 by the Korean Intellectual Property Office in counterpart Korean Patent Application No. 10-2014-0152859.

Communication dated Apr. 5, 2017 by the European Patent Office in counterpart European Patent Application No. 14192619.6.

Communication dated Sep. 21, 2017 by the Korean Intellectual Property Office in counterpart Korean Patent Application No. 10-2014-0152859.

* cited by examiner

RADIATION DETECTOR AND COMPUTED TOMOGRAPHY APPARATUS USING THE SAME

CROSS-REFERENCE TO RELATED APPLICATIONS

This application claims priority from Korean Patent Application No. 10-2013-0137188, filed on Nov. 12, 2013, and Korean Patent Application No. 10-2014-0152859, filed on Nov. 5, 2014, in the Korean Intellectual Property Office, the disclosures of which are incorporated herein in their entireties by reference.

BACKGROUND

1. Field

One or more embodiments of the present invention relate to a radiation detector, a tomography imaging apparatus using the same, and an X-ray imaging apparatus using the same, and more particularly, to a radiation detector, a tomography imaging apparatus using the same, and an X-ray imaging apparatus using the same, which count incident radiation photons to measure an amount of incident radiation.

One or more embodiments of the present invention relate in general to a radiation detector and a radiographic imaging system, such as a computed tomography (CT) apparatus, a positron emission tomography (PET) apparatus, a mammography apparatus or a single photon emission computed tomography (SPECT) apparatus or an X-ray system, or the like, using the radiation detector, and more particularly to a radiation detector and a radiographic imaging system using the radiation detector, which count incident radiation photons to measure an amount of incident radiation.

2. Description of the Related Art

Medical image processing apparatuses acquire an internal structure of an object as an image. Medical image processing apparatuses are noninvasive examination apparatuses that show the structural details, internal tissue, and fluid flow of a human body. A user such as a doctor diagnoses a health state and a disease of a patient by using a medical image output from a medical image processing apparatus.

Representative examples of apparatuses for irradiating radiation onto a patient to image an object include computed tomography (CT) apparatuses and X-ray apparatuses. Other types of apparatuses and systems also constitute representative examples of fields of use of or for the present invention, such as positron emission tomography (PET) apparatuses, mammography apparatuses and/or single photon emission computed tomography (SPECT).

Among medical image processing apparatuses, merely by way of example, CT apparatuses are referred to here, in that these provide a cross-sectional image of an object, and express the internal structures (for example, organs such as a kidney, a lung, etc.) of the object so as not to overlap each other unlike general X-ray apparatuses. Therefore, CT apparatuses are widely used for accurately diagnosing a disease.

An X-ray apparatus is a medical imaging apparatus that acquires images of internal structures of the human body by transmitting an X-ray through the human body. The X-ray apparatus may acquire medical images of a target object within a shorter time than other medical imaging apparatuses, as for example, an MRI apparatus and a CT apparatus. Therefore, the X-ray system is widely used in a chest imaging, abdomen imaging, skeleton imaging, nasal sinuses imaging, neck soft tissue imaging, and breast imaging.

Medical image processing apparatuses for irradiating radiation to image an object include a radiation detector that detects radiation passing through an object. Also, when the radiation passing through the object is detected sufficiently quickly and also sufficiently accurately, an accurate medical image can be reconstructed in a subsequent process of for instance image processing, based on radiation detected by the radiation detector. However, to achieve a sufficient resolution of reconstructed images, a sufficient amount of radiation having passed through the object must impinge on the detector.

Therefore, there is a need for a radiation detector and a medical image processing apparatus that not only quickly and accurately detect radiation passing through an object, but also detect sufficient amounts of radiation to enable reconstruction of images having high resolution. Combining these objectives has in the past eluded the skilled persons in the technical field of the present invention.

SUMMARY

One or more embodiments of the present invention include a radiation detector, a tomography imaging apparatus using the same, and an X-ray imaging apparatus using the same, which quickly and accurately detect radiation passing through an object.

One or more embodiments of the present invention include a radiation detector, a tomography imaging apparatus using the same, and an X-ray imaging apparatus using the same, which quickly count radiation photons passing through an object to accurately detect an amount of radiation.

Additional aspects will be set forth in part in the description which follows and, in part, will be apparent from the description, or may be learned by practice of the presented embodiments.

According to one or more embodiments of the present invention, a radiation detector for sensing radiation includes a plurality of image pixels that each include at least one counting pixel, and restore an image, wherein, the at least one counting pixel includes: a radiation absorption layer that converts incident photons into an electrical signal; and a photon processor that counts number of the photons, based on the electrical signal transferred from the radiation absorption layer, and number of the image pixels is smaller than number of the counting pixels.

The at least one counting pixel may count number of photons smaller than number of photons incident on a corresponding image pixel.

The photon processor may count the number of photons based on the electrical signal according to a direct method that directly converts the incident photons into an electric charge to detect the photons.

Each of the plurality of image pixels may correspond to one pixel value constituting the image.

Each of the plurality of image pixels may include a plurality of the counting pixels.

Each of the plurality of image pixels may be a pixel which is used to calculate one pixel value included in the image, based on number of photons counted by the plurality of counting pixels.

The photon processor may include a counting memory that counts and stores number of photons smaller than number of photons which are incident on a corresponding image pixel for a certain time.

The photon processor may include: a comparator that compares the electrical signal with a reference value to determine whether the electrical signal exceeds the reference value; and a counting memory that counts and stores number of photons exceeding the reference value, based on a comparison result of the comparator.

The at least one counting pixel may include a counting memory that counts and stores number of photons smaller than number of photons which are incident on a corresponding image pixel for a certain time.

When each of the plurality of image pixels corresponds to a pixel of the radiation detector, the at least one counting pixel included in the pixel may be divided into at least one counting pixel group, and number of photons counted by the at least one counting pixel group may correspond to one image pixel value in the image.

Number of the counting pixel groups may be equal to or more than number of the pixels.

A size of the at least one counting pixel group may be equal to or smaller than a size of the pixel.

When each of the plurality of image pixels corresponds to a pixel of the radiation detector, a plurality of the counting pixels included in a plurality of adjacent pixels may be divided into at least one counting pixel group, and number of photons counted by each of the plurality of counting pixel groups may correspond to one image pixel value in the image.

The radiation detector may be a radiation detector used to generate a tomography image.

The radiation detector may sense radiation which is emitted from an X-ray source, which is attached to a gantry and rotates, and has passed through an object.

The radiation detector may be a radiation detector used to generate an X-ray image.

The radiation detector may sense radiation that is emitted from an X-ray source, which is attached to a moving apparatus and is adjusted in position, and has passed through an object.

The radiation absorption layer may be formed of cadmium telluride (CdTe).

According to one or more embodiments of the present invention, a radiation detector includes a plurality of pixels which sense radiation. Each of the plurality of pixels including a plurality of counting pixels that sense the radiation for restoring an image, wherein, each of the plurality of counting pixels includes: a radiation absorption layer that converts incident photons into an electrical signal; and a photon processor that counts number of the photons, based on the electrical signal.

The photon processor may include a counting memory that stores a counted value.

Each of the plurality of counting pixels may count number of photons smaller than number of photons incident on a corresponding pixel.

The radiation detector may be used to generate a tomography image.

Each of the plurality of pixels may absorb and count two hundred million or more photons per second.

Each of the plurality of pixels may include 24, 25, or 36 counting pixels.

The number of photons counted by the counting pixel may correspond to one image pixel value in the image.

A total number of photons, counted by a counting pixel group including a plurality of counting pixels which are included in the pixel and are arranged adjacent to each other, may correspond to one image pixel value in the image.

A plurality of counting pixels included in a plurality of adjacent pixels may be divided into a plurality of groups, and total number of photons counted by each of the plurality of groups may correspond to one image pixel value in the image.

The photon processor may further include: a comparator that compares the electrical signal with a reference value to determine whether the electrical signal exceeds the reference value; and a counting memory that counts and stores the number of photons exceeding the reference value.

According to one or more embodiments of the present invention, a tomography imaging apparatus includes: a radiation detector that includes a plurality of image pixels that each include at least one counting pixel, and restore an image; and an image processor that reconstructs a tomography image, based on number of photons sensed by the radiation detector, wherein, the at least one counting pixel includes: a radiation absorption layer that converts incident photons into an electrical signal; and a photon processor that counts number of the photons, based on the electrical signal transferred from the radiation absorption layer, and number of the image pixels is smaller than number of the counting pixels.

According to one or more embodiments of the present invention, an X-ray imaging apparatus includes: a radiation detector that includes a plurality of pixels that each include at least one counting pixel, and restore an image; and an image processor that reconstructs a tomography image, based on number of photons sensed by the radiation detector, wherein, the at least one counting pixel includes: a radiation absorption layer that converts incident photons into an electrical signal; and a photon processor that counts number of the photons, based on the electrical signal transferred from the radiation absorption layer, and number of the pixels is smaller than number of the counting pixels.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1A:
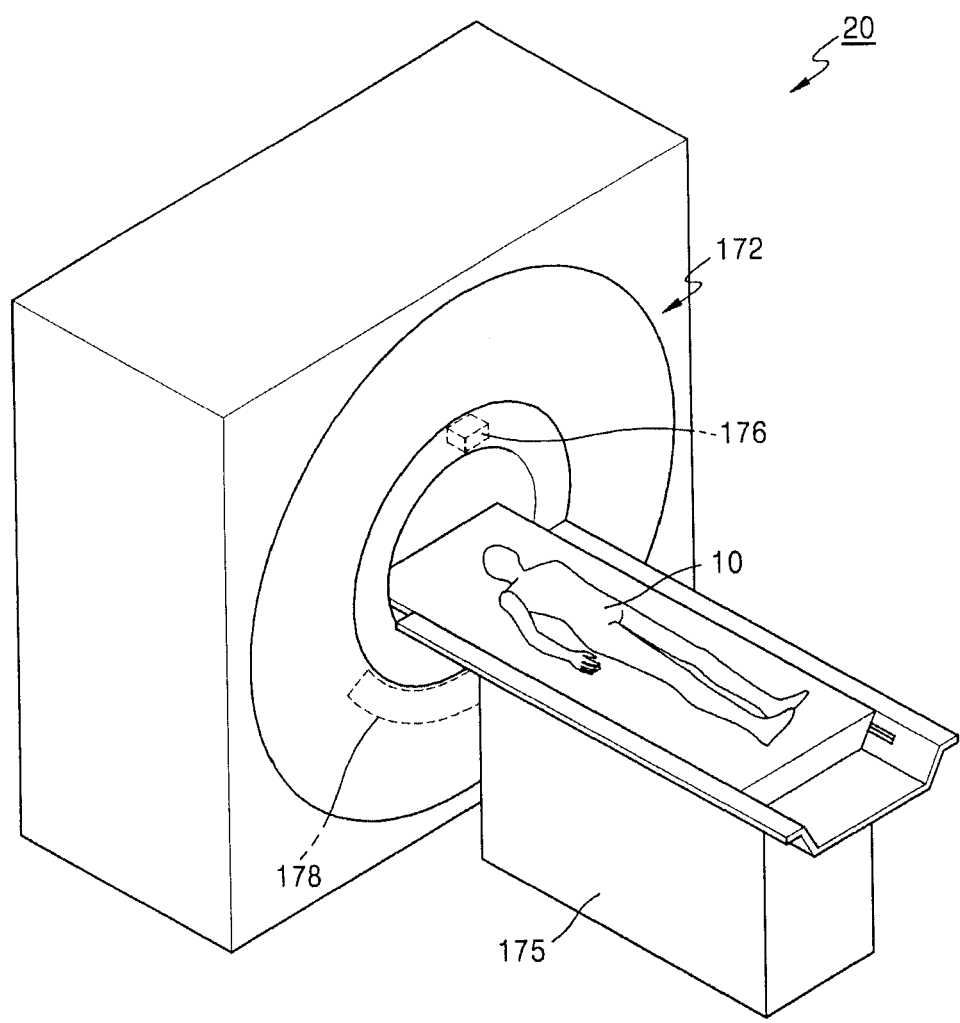
FIG. 1A is a schematic diagram of a general CT system.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. Expressions such as "at least one of," when preceding a list of elements, modify the entire list of elements and do not modify the individual elements of the list.

Advantages and features of one or more embodiments of the present invention and methods of accomplishing the same may be understood more readily by reference to the following detailed description of the embodiments and the accompanying drawings. In this regard, the present embodiments may have different forms and should not be construed as being limited to the descriptions set forth herein. Rather, these embodiments are provided so that this disclosure will be thorough and complete and will fully convey the concept of the present embodiments to one of ordinary skill in the art, and the present invention will only be defined by the appended claims. Like reference numerals refer to like elements throughout the specification.

Hereinafter, the terms used in the specification will now be briefly defined, and the embodiments will now be described in detail.

All terms including descriptive or technical terms which are used herein should be construed as having meanings that are obvious to one of ordinary skill in the art. However, the terms may have different meanings according to an intention of one of ordinary skill in the art, precedent cases, or the appearance of new technologies. Also, some terms may be arbitrarily selected by the applicant, and in this case, the meaning of the selected terms will be described in detail in the detailed description of the invention. Thus, the terms used herein have to be defined based on the meaning of the terms together with the description throughout the specification.

When a part "includes" or "comprises" an element, unless there is a particular description contrary thereto, the part can further include other elements, not excluding the other elements. Also, the term 'unit' in the embodiments of the present invention means a software component or hardware components such as a field-programmable gate array (FPGA) or an application-specific integrated circuit (ASIC), and performs a specific function. However, the term 'unit' is not limited to software or hardware. The 'unit' may be formed so as to be in an addressable storage medium, or may be formed so as to operate one or more processors. Thus, for example, the term 'unit' may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and 'units' may be associated with a smaller number of components and 'units', or may be divided into additional components and 'units'.

Reference will now be made in detail to embodiments, examples of which are illustrated in the accompanying drawings. In this regard, the present embodiments may have different forms and should not be construed as being limited to the descriptions set forth herein. In the following description, well-known functions or constructions are not described in detail since they would obscure the embodiments with unnecessary detail.

Expressions such as "at least one of," when preceding a list of elements, modify the entire list of elements and do not modify the individual elements of the list.

Throughout the specification, an "image" may mean multi-dimensional data formed of discrete image elements (e.g., pixels in a two-dimensional (2D) image and voxels in a three-dimensional (3D) image). For example, the image may include a medical image of an object which is captured by a computed tomography (CT) image-capturing apparatus.

Throughout the specification, a "CT image" may mean an image generated by synthesizing a plurality of X-ray images that are obtained by imaging an object while a CT image-capturing apparatus rotates around at least one axis with respect to the object.

Throughout the specification, an "object" may include a human, an animal, or a part of a human or animal. For example, the object may include organs such as the liver, the heart, the womb, the brain, a breast, the abdomen, or the like, or a blood vessel. Also, the object may include a phantom. The phantom means a material having a volume that is very close to a density and effective atomic number of an organism, and may include a sphere phantom having a characteristic similar to a physical body.

Throughout the specification, a "user" may be, but is not limited to, a medical expert including a doctor, a nurse, a medical laboratory technologist, a medial image expert, and a technician who repairs a medical apparatus.

Since a CT system is capable of providing a cross-sectional image of an object, the CT system may express an inner structure (e.g., an organ such as a kidney, a lung, etc.) of the object without an overlap therebetween, compared to a general X-ray capturing apparatus.

The CT system may obtain a plurality of pieces of image data with a thickness that is not more than 2 mm for several tens to several hundreds of times per second and then may process the plurality of pieces of image data, so that the CT system may provide a relatively accurate cross-sectional image of the object. According to the related art, only a horizontal cross-sectional image of the object can be obtained, but this issue has been overcome due to various image reconstruction methods. Examples of 3D image reconstruction methods are:

- A shaded surface display (SSD) method: The SSD method is an initial 3D imaging method that only displays voxels having a predetermined Hounsfield Units (HU) value.
- A maximum intensity projection (MIP)/minimum intensity projection (MinIP) method: The MIP/MinIP method is a 3D imaging method that only displays voxels having the greatest or smallest HU value from among voxels that construct an image.
- A volume rendering (VR) method: The VR method is an imaging method capable of adjusting a color and transmittance of voxels that construct an image, according to interest areas.

A virtual endoscopy method: This method allows an endoscopy observation in a 3D image that is reconstructed by using the VR method or the SSD method.

A multi-planar reformation (MPR) method: The MPR method is used to reconstruct an image into a different cross-sectional image. A user may reconstruct an image in every desired direction.

An editing method: This method involves editing adjacent voxels so as to allow a user to easily observe an interest area in volume rendering.

A voxel of interest (VOI) method: The VOI method only displays a selected area in volume rendering.

A CT system 20 according to an embodiment of the present invention will now be described with reference to FIG. 1A. The CT system 20 may include devices having various forms. The present invention may relate, as an alternative for the exhibited CT system 20, to other radiographic imaging systems. For example, the invention may relate to an X-ray system, a positron emission tomography (PET) apparatus, a mammography apparatus or a single photon emission computed tomography (SPECT) apparatus. Also therein images of objects can be generated or reconstructed based on detections of emitted and more or less transmitted radiation, where such detections may be obtained by radiation detectors, which are sensitive to energy levels and may count photons.

FIG. 1A schematically illustrates by way of example of an embodiment, a CT system 20. Referring to FIG. 1A, the CT system 20 may include a gantry 172, a table 175, an X-ray generating unit 176, and an X-ray detecting unit 178.

The gantry 172 may include the X-ray generating unit 176 and the X-ray detecting unit 178.

An object 10 may be positioned on the table 175.

The table 175 may move in a predetermined direction (e.g., at least one of up and down-right and left directions) during a CT imaging procedure. Also, the table 175 may tilt or rotate by a predetermined degree in a predetermined direction.

The gantry 172 may also tilt by a predetermined degree in a predetermined direction.

Figure 1B:
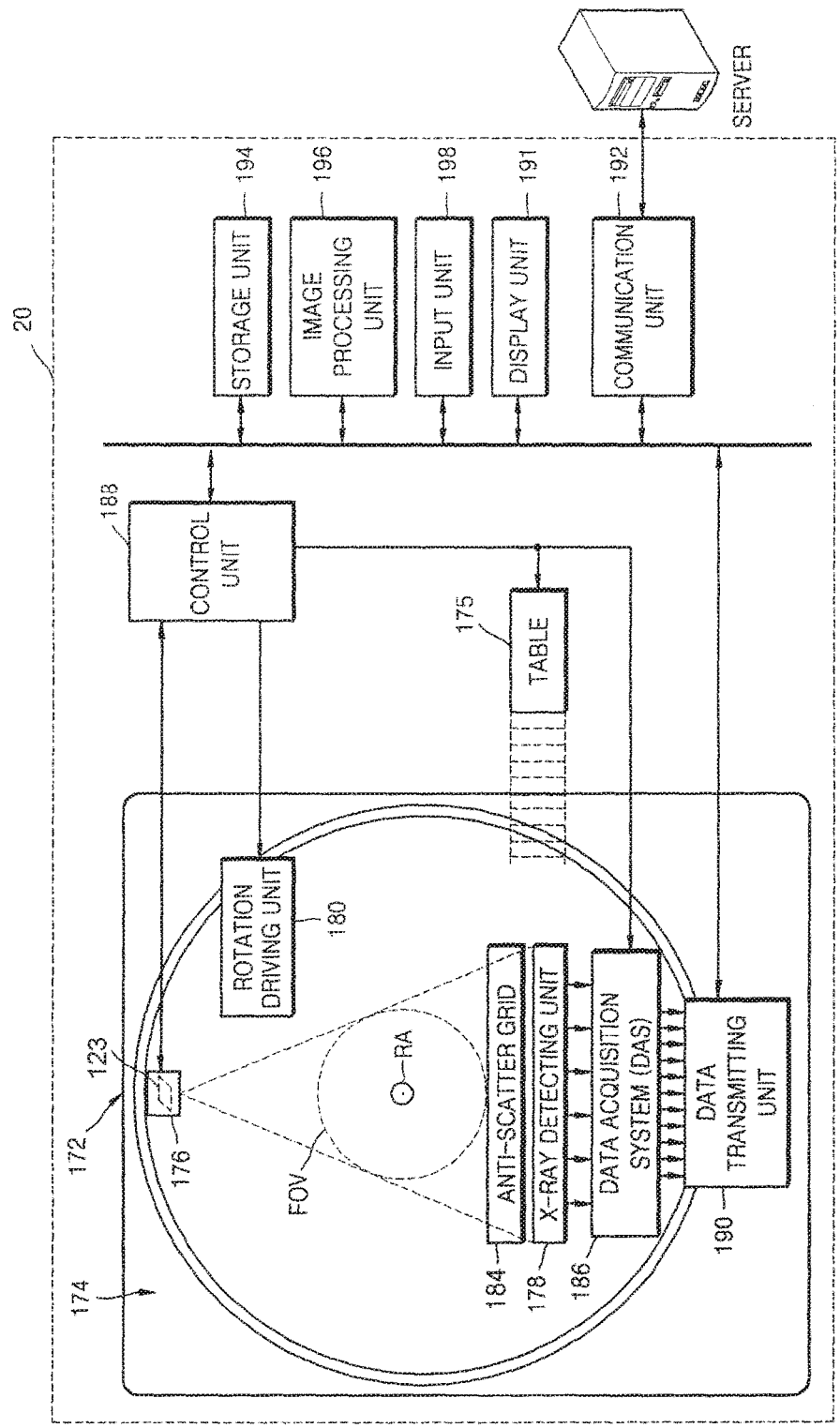
FIG. 1B is a diagram illustrating a structure of a CT system according to an embodiment of the present invention.

FIG. 1B is a diagram illustrating a structure of the CT system 20.

The CT system 20 may include the gantry 172, the table 175, a control unit 188, a storage unit 194, an image processing unit 196, an input unit 198, a display unit 191, and a communication unit 192, which may enable communications to a server 162 or the like.

As described above, the object 10 may be positioned on the table 175. In the present embodiment, the table 175 may move in a predetermined direction (e.g., at least one of up, down, right, and left directions) through control by the control unit 188.

The gantry 172 may include a rotating frame 174, the X-ray generating unit 176, the X-ray detecting unit 178, a rotation driving unit 180, a data acquisition system (DAS) 186, and a data transmitting unit 190.

The gantry 172 may include the rotating frame 174 having a loop shape capable of rotating with respect to a predetermined rotation axis RA. Also, the rotating frame 174 may have a disc shape.

The rotating frame 174 may include the X-ray generating unit 176 and the X-ray detecting unit 178 that face each other so as to have predetermined field of views FOV. The rotating frame 174 may also include an anti-scatter grid 184. The anti-scatter grid 184 may be positioned between the X-ray generating unit 176 and the X-ray detecting unit 178.

In a medical imaging system, X-ray radiation that reaches a detector (or a photosensitive film) includes not only attenuated primary radiation that forms a valuable image but also includes scattered radiation that deteriorates a quality of an image. In order to transmit the primary radiation and to attenuate the scattered radiation, the anti-scatter grid 184 may be positioned between a patient and the detector (or the photosensitive film).

For example, the anti-scatter grid 184 may be formed by alternately stacking lead foil strips and an interspace material such as a solid polymer material, solid polymer, or a fiber composite material. However, formation of the anti-scatter grid 184 is not limited thereto.

The rotating frame 174 may receive a driving signal from the rotation driving unit 180 and may rotate the X-ray generating unit 176 and the X-ray detecting unit 178 by a predetermined rotation speed. The rotating frame 174 may receive the driving signal and power from the rotation driving unit 180 while the rotating frame 174 contacts the rotation driving unit 180 via a slip ring (not shown). Also, the rotating frame 174 may receive the driving signal and power from the rotation driving unit 180 via wireless communication.

The X-ray generating unit 176 may receive a voltage and current from a power distribution unit (PDU) (not shown) via a slip ring (not shown) and then a high voltage generating unit (not shown), and then may generate and emit X-rays. When the high voltage generating unit applies a predetermined voltage (hereinafter, referred as the tube voltage) to the X-ray generating unit 176, the X-ray generating unit 176 may generate X-rays having a plurality of energy spectrums that correspond to the tube voltage.

The X-rays generated by the X-ray generating unit 176 may have a predetermined form due to a collimator 123 and then may be emitted.

The X-ray detecting unit 178 may be positioned to face the X-ray generating unit 176. The X-ray detecting unit 178 may include a plurality of X-ray detecting devices. Each of the plurality of X-ray detecting devices may establish one channel but one or more embodiments of the present invention are not limited thereto.

The X-ray detecting unit 178 may detect the X-rays that are generated by the X-ray generating unit 176 and that is transmitted via the object 10, and may generate an electrical signal corresponding to the intensity of the detected X-rays.

The present application relates to a direct-type X-ray detecting unit for detecting radiation by directly converting the radiation into electric charges. The direct-type X-ray detecting unit may use a photon counting detector. The DAS 186 may be connected to the X-ray detecting unit 178. The electrical signal generated by the X-ray detecting unit 178 may be collected by the DAS 186, by a wired connection or wirelessly.

According to a slice thickness or the number of slices, only some of a plurality of pieces of data collected by the X-ray detecting unit 178 may be provided to the image processing unit 196 via the data transmitting unit 190, or the image processing unit 196 may select only some of the plurality of pieces of data.

The electrical signal may be provided to the image processing unit 196 as the digital signal via the data transmitting unit 190. The digital signal may be provided to the image processing unit 196 via a wired connection or wirelessly.

The control unit 188 may control an operation of each of the parts, elements, components or modules in the CT system 20. For example, the control unit 188 may control operations of the table 175, the rotation driving unit 180, the collimator 123, the DAS 186, the storage unit 194, the image processing unit 196, the input unit 198, the display unit 191, the communication unit 192, or the like.

The image processing unit 196 may receive data (e.g., pure data before a processing operation), which is obtained from the DAS 186, via the data transmitting unit 190, and may perform pre-processing.

The pre-processing may include a process of correcting sensitivity irregularity between channels, a process of correcting a signal loss due to a rapid decrease of signal strength or due to an X-ray absorbing material such as metal or the like.

Data output from the image processing unit 196 may be referred as raw data or projection data. The projection data and image-capturing conditions (e.g., the tube voltage, an image-capturing angle, etc.) during obtainment of the data may be stored together in the storage unit 194.

The projection data may be a group of data values that correspond to the intensity of the X-rays from the assembly including an X-ray source 122 (refer to FIG. 3A) and a collimator 123 that pass through the object 10 and is detected by the X-ray detecting unit 178. For convenience of description, it is assumed that a group of a plurality of pieces of projection data that are simultaneously obtained from all channels by a same image-capturing degree is referred as a projection data set.

The storage unit 194 may include at least one storage medium from among a flash memory-type storage medium, a hard disk-type storage medium, a multimedia card micro-type storage medium, card-type memories (e.g., an SD card, an XD memory, and the like), Random Access Memory (RAM), Static Random Access Memory (SRAM), Read-Only Memory (ROM), Electrically Erasable Programmable Read-Only Memory (EEPROM). Programmable Read-Only Memory (PROM) magnetic memory, a magnetic disc, and an optical disc.

The image processing unit 196 may reconstruct a cross-sectional image with respect to the object 10 by using the projection data set. The cross-sectional image may be a 3D image. In other words, the image processing unit 196 may reconstruct the 3D image of the object 10 by using a cone beam reconstruction method or the like, based on the projection data set.

The input unit 198 may receive an external input with respect to an X-ray tomography imaging condition, an image processing condition, or the like. For example, the X-ray tomography imaging condition may include tube voltages, energy value setting with respect to a plurality of X-rays, selection of an image-capturing protocol, selection of an image reconstruction method, setting of a FOV area, the number of slices, a slice thickness, parameter setting with respect to image post-processing, or the like. Also, the image processing condition may include resolution of an image, attenuation coefficient setting with respect to the image, setting of an image combining ratio, or the like.

The input unit 198 may include a device for receiving a predetermined input from an external source. For example, the input unit 198 may include a microphone, a keyboard, a mouse, a joystick, a touch pad, a touch pen, a voice recognition device, a gesture recognition device, or the like.

The display unit 191 may display an X-ray tomography image reconstructed by the image processing unit 196.

Exchanges of data, power, or the like between the aforementioned elements may be performed by using at least one of wired communication, wireless communication, and/or optical communication.

The communication unit 192 may perform communication with an external device, an external medical apparatus, etc. via a server 162 or the like. The communication will now be described with reference to FIG. 2.

Figure 2:
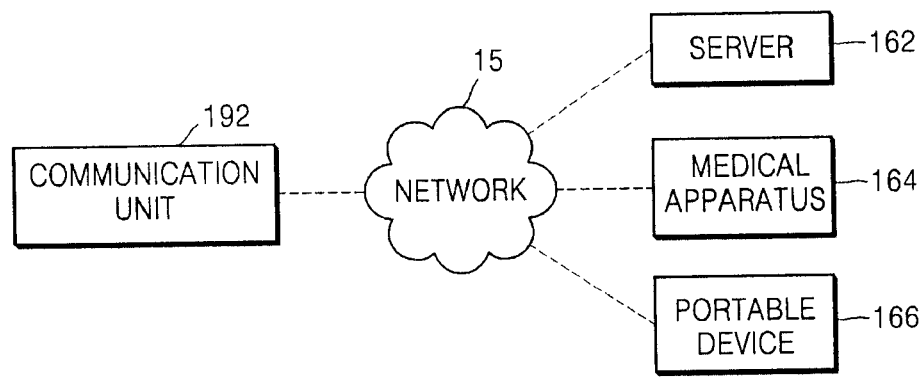
FIG. 2 is a diagram illustrating a configuration of a communication unit.

FIG. 2 is a diagram illustrating a structure of the communication unit 192.

The communication unit 192 may be connected to a network 15 by a wired connection or wirelessly and therefore may perform communication with the server 162, an external medical apparatus 164, or an external portable device 166. The communication unit 192 may exchange data with a hospital server or other medical apparatuses in a hospital connected via a Picture Archiving and Communication System (PACS). Also, the communication unit 192 may perform data communication with the portable device 166 or the like, according to a Digital Imaging and Communications in Medicine (DICOM) standard.

The communication unit 192 may transmit and receive data related to diagnosing the object 10 via the network 15. Also, the communication unit 192 may transmit and receive a medical image obtained from the external medical apparatus 164 such as a magnetic resonance imaging (MRI) apparatus, an X-ray apparatus, or the like.

Furthermore, the communication unit 192 may receive a diagnosis history or a medical treatment schedule of a patient from the server 162 and may use the diagnosis history or the medical treatment schedule in a clinical diagnosis of the patient. Also, the communication unit 192 may perform data communication with not only the server 162 or the external medical apparatus 164 in a hospital but also with the portable device 166, for instance of a user or of a patient. The communication unit 192 may also obtain control parameters as mentioned above in relation to the input unit 198, and consequently in an embodiment the input unit 198 and the communication unit 192 may be combined.

Also, the communication unit 192 may transmit information about a device error, information about a quality control status, or the like to a system manager or a service manager via the network 15, and may receive feedback corresponding to the information.

Figure 3A:
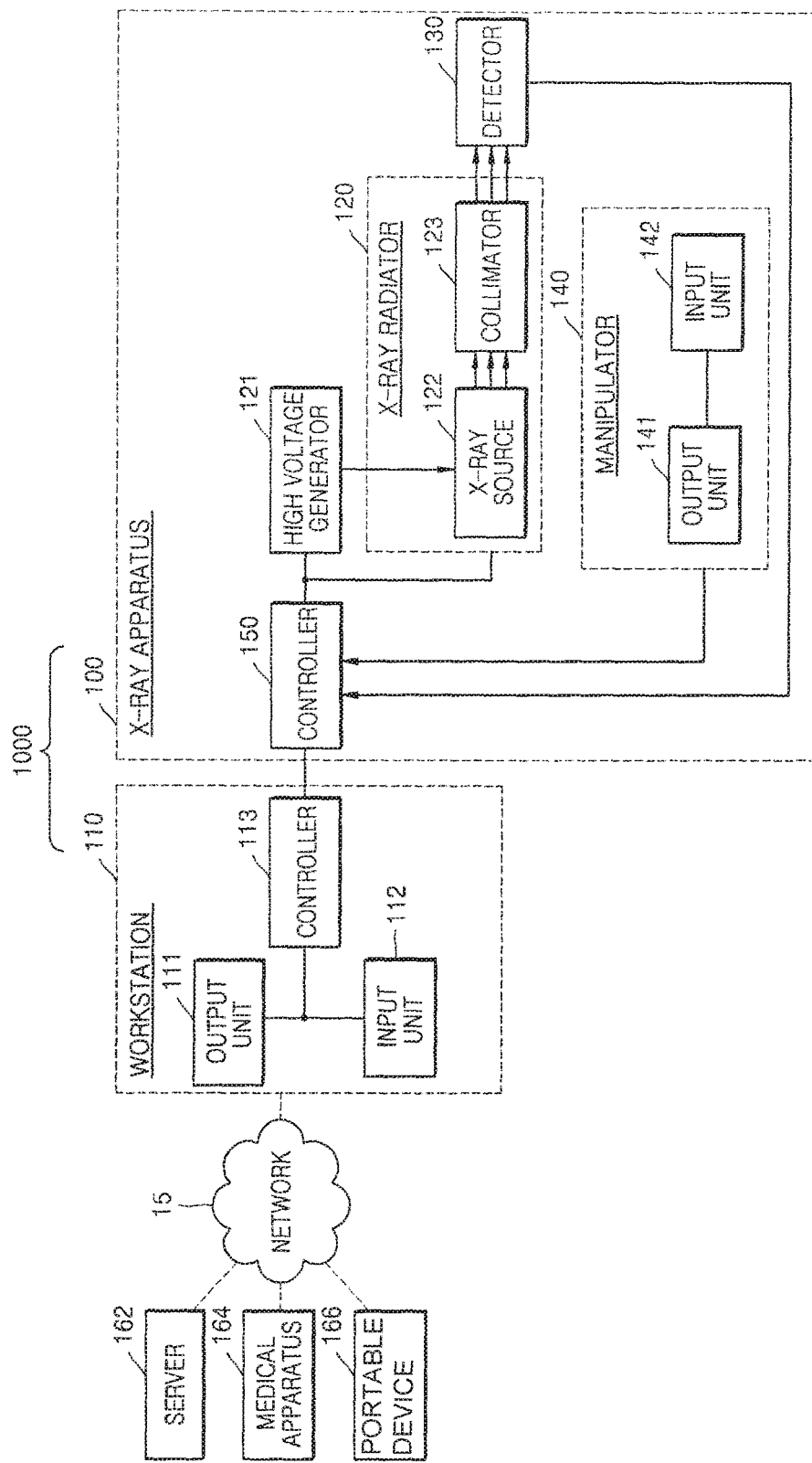
FIG. 3A is a diagram illustrating a configuration of an X-ray system.

FIG. 3A is a diagram illustrating a configuration of an X-ray system 1000.

Referring to FIG. 3A, the X-ray system 1000 includes an X-ray apparatus 100 and a workstation 110. The X-ray apparatus 100 illustrated in FIG. 3A may be a fixed-type X-ray apparatus or a mobile X-ray apparatus. The X-ray apparatus 100 may include an X-ray irradiation unit 120, i.e., an X-ray radiator, a high voltage generator 121, a detector 130, a manipulation unit 140, i.e., a manipulator, and a control unit 150, i.e., a controller. The control unit 150 may control an overall operation of the X-ray apparatus 100.

The high voltage generator 121 generates a high voltage used to generate X-rays, and applies the high voltage to an X-ray source 122.

The X-ray irradiation unit 120 includes the X-ray source 122, which receives the high voltage applied from the high voltage generator 121 to generate and irradiate the X-rays, and a collimator 123 that guide a path of the X-rays irradiated from the X-ray source 122 to adjust an irradiation region of the X-ray.

The X-ray source 122 includes an X-ray tube that may be realized as a diode including a cathode and an anode. An inside of the X-ray tube is set as a high vacuum state of about 10 mmHg, and a filament of the cathode is heated to a high temperature to generate thermal electrons. The filament may be a tungsten filament, and a voltage of about 10 V and a current of 3 to 5 A may be applied to an electric wire connected to the filament to heat the filament.

In addition, when a high voltage of about 10 to about 300 kVp is applied between the cathode and the anode, the thermal electrons are accelerated to crash onto a target material of the anode, and then, X-rays are generated. The X-rays are irradiated to outside via a window, and the window may be formed as a beryllium thin film. Here, most of the energy of the electrons colliding with the target material is consumed as heat, and remaining energy is converted into the X-rays.

The anode is mainly formed of copper, and the target material is disposed at an opposite side to the anode. The target material may be a high resistive material such as Cr, Fe, Co, Ni, W, or Mo. The target material may be rotated by a rotating field. When the target material is rotated, an electron impact area is increased, and a heat accumulation rate per unit area may be increased ten times greater than that of a case where the target material is fixed.

The voltage applied between the cathode and the anode of the X-ray tube is referred to as a tube voltage, and the tube voltage is applied from the high voltage generator 121 and a magnitude of the tube voltage may be expressed by a crest value (kVp). When the tube voltage increases, a velocity of the thermal electrons increases, and accordingly, energy of the X-rays (energy of photon) that are generated when the thermal electrons collide with the target material is increased. The current flowing in the X-ray tube is referred to as a tube current that may be expressed as an average value (mA). When the tube current increases, the number of thermal electrons emitted from the filament is increased, and accordingly, a dose of the X-rays (the number of X-ray photons) generated when the thermal electrons collide with the target material is increased.

Therefore, the energy of the X-rays may be adjusted according to the tube voltage, and the intensity or dose of the X-rays may be adjusted according to the tube current and the X-ray exposure time.

The detector 130 detects the X-rays that are irradiated from the X-ray irradiation unit 120 and have passed through an object 10. The detector 130 may be a digital detector. The detector 130 may be implemented with a thin film transistor (TFT) or a charge coupled device (CCD). In FIG. 3A, the detector 130 is illustrated as being included in the X-ray apparatus 100, but the detector 130 may be an X-ray detector that is a separate apparatus which is detachably connected to the X-ray apparatus 100.

Moreover, the X-ray apparatus 100 may further include the manipulation unit 140 that provides an interface for manipulating the X-ray apparatus 100. The manipulation unit 140 may include an output unit 141 and an input unit 142. The input unit 142 may receive, from a user, a command for manipulating the X-ray apparatus 100 and various pieces of information about X-ray imaging. The control unit 150 may control or manipulate the X-ray apparatus 100, based on information input to the input unit 142. The output unit 141 may output sound indicating imaging-related information such as irradiation of X-rays under a control of the control unit 150.

The workstation 110 and the X-ray apparatus 100 may be connected to each other by wire or wirelessly. If they are wirelessly connected to each other, a device (not shown) for synchronizing clocks with each other may be further included. The workstation 110 may be disposed in a space which is physically separated from the X-ray apparatus 100.

The workstation 110 may include an output unit 111, an input unit 112, and a control unit 113, i.e., a controller. The output unit 111 and the input unit 112 provide a user with an interface for manipulating the workstation 110 and the X-ray apparatus 100. The control unit 113 may control the workstation 110 and the X-ray apparatus 100.

The X-ray apparatus 100 may be controlled through the workstation 110, and may also be controlled by the control unit 150 included in the X-ray apparatus 100. Therefore, the user may control the X-ray apparatus 100 through the workstation 110, or control the X-ray apparatus 100 by using the manipulation unit 140 and the control unit 150 which are included in the X-ray apparatus 100. In other words, the user may remotely control the X-ray apparatus 100 through the workstation 110, or may directly control the X-ray apparatus 100.

In FIG. 3A, the control unit 113 of the workstation 110 and the control unit 150 of the X-ray apparatus 100 are separately illustrated, but FIG. 3A is merely an example. As another example, the control units 113 and 150 may be implemented as one integrated control unit, which may be included in only one selected from the workstation 110 and the X-ray apparatus 100. Hereinafter, the control units 113 and 150 denote the control unit 113 of the workstation 110 and/or the control unit 150 of the X-ray apparatus 100.

The output unit 111 and input unit 112 of the workstation 110 and the output unit 141 and input unit 142 of the X-ray apparatus 100 may each provide the user with the interface for manipulating the X-ray apparatus 100. In FIG. 3A, it is illustrated that the workstation 110 includes the output unit 111 and the input unit 112 and the X-ray apparatus 100 includes the output unit 141 and the input unit 142, but the present embodiment is not limited thereto. As another example, an output unit or an input unit may be included in only one selected from the workstation 110 and the X-ray apparatus 100.

Hereinafter, the input units 112 and 142 denote the input unit 112 of the workstation 110 and/or the input unit 142 of the X-ray apparatus 100, and the output units 111 and 141 denote the output unit 111 of the workstation 110 and/or the output unit 141 of the X-ray apparatus 100.

Each of the input units 112 and 142 may include, for example, a keyboard, a mouse, a touch screen, a voice recognizer, a fingerprint recognizer, and an iris recognizer, and may include an input device well known to those of ordinary skill in the art. The user may input a command for irradiating the X-rays via the input units 112 and 142, and to do this, each of the input units 112 and 142 may include a switch for inputting the command. The switch may be configured so that an irradiation command for irradiating the X-rays may be input only when the switch is pushed twice.

That is, when the user pushes the switch, a prepare command for performing a pre-heating operation for X-ray irradiation may be input through the switch, and then, when the user pushes the switch once more, the irradiation command for irradiating the X-rays may be substantially input through the switch. When the user manipulates the switch as described above, each of the control units 113 and 150 generates a signal (i.e., a prepare signal) corresponding to a command input through the switch manipulation, and outputs the generated signal to the high voltage generator 121 that generates a high voltage for generating the X-rays.

When the high voltage generator 121 receives the prepare signal output from the control units 113 and 150, the high voltage generator 121 starts a pre-heating operation, and when the pre-heating is finished, the high voltage generator 121 outputs a ready signal to the control units 113 and 150. In addition, the detector 130 also needs to prepare for detecting the X-rays, and thus, the control units 113 and 150 transfer the prepare signal to the detector 130 at the same time of pre-heating of the high voltage generator 121, so that the detector 130 prepares for detecting the X-rays transmitted through the object 10. The detector 130 prepares for detecting the X-rays when the prepare signal is received, and when the preparing for the detection is finished, the detector 130 transfers a detection ready signal to the control units 113 and 150.

When the pre-heating operation of the high voltage generator 121 is finished, the detector 130 is ready for detecting the X-rays, and the control units 113 and 150 transfer the irradiation signal to the high voltage generator 121. Therefore, the high voltage generator 121 generates the high voltage to apply the high voltage to the X-ray source 122, and the X-ray source 122 irradiates the X-rays.

In transferring the irradiation signal, the control units 113 and 150 may transfer a sound output signal to the output units 111 and 141 so that the output units 111 and 141 output certain sound. Also, the output units 111 and 141 may output sound representing other information relating to the imaging, in addition to the X-ray irradiation. In FIG. 3A, the output unit 141 is illustrated as being included in the manipulation unit 140, but the present embodiment is not limited thereto. The output unit 141 or a portion of the output unit 141 may be located at a different position from the manipulation unit 140. For example, the output unit 141 may be located on a wall surface of an examination room in which the X-ray imaging of the object 10 is performed.

The control units 113 and 150 control positions of the X-ray irradiation unit 120 and the detector 130, an imaging timing, and imaging conditions according to imaging conditions set by the user.

In detail, the control units 113 and 150 control the high voltage generator 121 and the detector 130 according to the command input via the input units 112 and 142 so as to control an irradiation timing of the X-rays, an intensity of the X-rays, and an irradiation region of the X-rays. Also, the control units 113 and 150 adjust the position of the detector 130 according to an imaging condition, and control an operation timing of the detector 130.

In addition, the control units 113 and 150 generate a medical image of the object 10 by using image data transmitted from the detector 130. In particular, the control units 113 and 150 receive the image data from the detector 130, and then generate the medical image of the object 10 by removing noise in the image data and adjusting a dynamic range and interleaving of the image data.

The output units 111 and 114 may output a medical image generated by the control units 113 and 150. The output units 111 and 114 may output information that is necessary for the user to manipulate the X-ray apparatus 100, for example, a user interface (UI), user information, or object information. Examples of the output units 111 and 114 may include a printer, a cathode ray tube (CRT) display, a liquid crystal display (LCD), a plasma display panel (PDP), an organic light emitting diode (OLED) display, a field emission display (FED), a light emitting diode (LED) display, a vacuum fluorescent display (VFD), a digital light processing (DLP) display, a primary flight display (PFD), a three-dimensional (3D) display, a transparent display, and other various output devices well known in the art.

The workstation 110 shown in FIG. 3A may further include a communication unit (not shown) that may be connected to a server 162, a medical apparatus 164, and a portable device 166 via a network 15.

The communication unit may be connected to the network 15 via wires or wirelessly to communicate with the external server 162, the external medical apparatus 164, or the external portable device 166. The communication unit may transmit or receive data relating to diagnosis of the object 10 via the network 15, and may transmit or receive medical images captured by the other medical apparatus 164, for example, a CT, an MRI or an X-ray apparatus. Moreover, the communication unit may receive medical history or treatment schedule of an object 10 (e.g., a patient) from the server 162 to diagnose a disease of the object 10. Also, the communication unit may perform data communication with the portable device 166 such as a mobile phone of a doctor or a patient, a personal digital assistant (PDA), or a laptop computer, as well as the server 162 or the medical apparatus 164 in a hospital.

The communication unit may include one or more elements enabling to communicate with external apparatuses, for example, a short distance communication module, a wired communication module, and a wireless communication module.

The short distance communication module is a module for communicating with a device located within a predetermined distance. The short distance communication technology may be wireless local area network (LAN), Wi-Fi, Bluetooth, Zigbee, Wi-Fi Direct (WFD), ultra wideband (UWD), infrared data association (IrDA), Bluetooth low energy (BLE), near field communication (NFC), or the like; however, the embodiments of the present invention are not limited thereto.

The wired communication module is a module for communicating by using an electric signal or an optical signal, and the wired communication technology may be wired communication technology using a pair cable, a coaxial cable, or an optical fiber cable, and a wired communication technology that is well known in the art.

The wireless communication module may transmit/receive a wireless signal to/from at least one of a base, an external device, and a server in a mobile communication network. Here, the wireless signal may be a voice call signal, a video call signal, or various types of data according to text/multimedia messages transmission.

The X-ray apparatus 100 shown in FIG. 3A may include a plurality of digital signal processors (DSPs), an ultra-small calculator, and a processing circuit for specialized usage (for example, a high speed analog/digital (A/D) conversion, a high speed Fourier transformation, an array process, etc.).

In addition, the communication between the workstation 110 and the X-ray apparatus 100 may use a high speed digital interface, such as low voltage differential signaling (LVDS), asynchronous serial communication, such as universal asynchronous receiver transmitter (UART), synchronous serial communication, or a low latency network protocol, such as a controller area network (CAN), and other various communication methods that are well known in the art may be used.

Figure 3B:
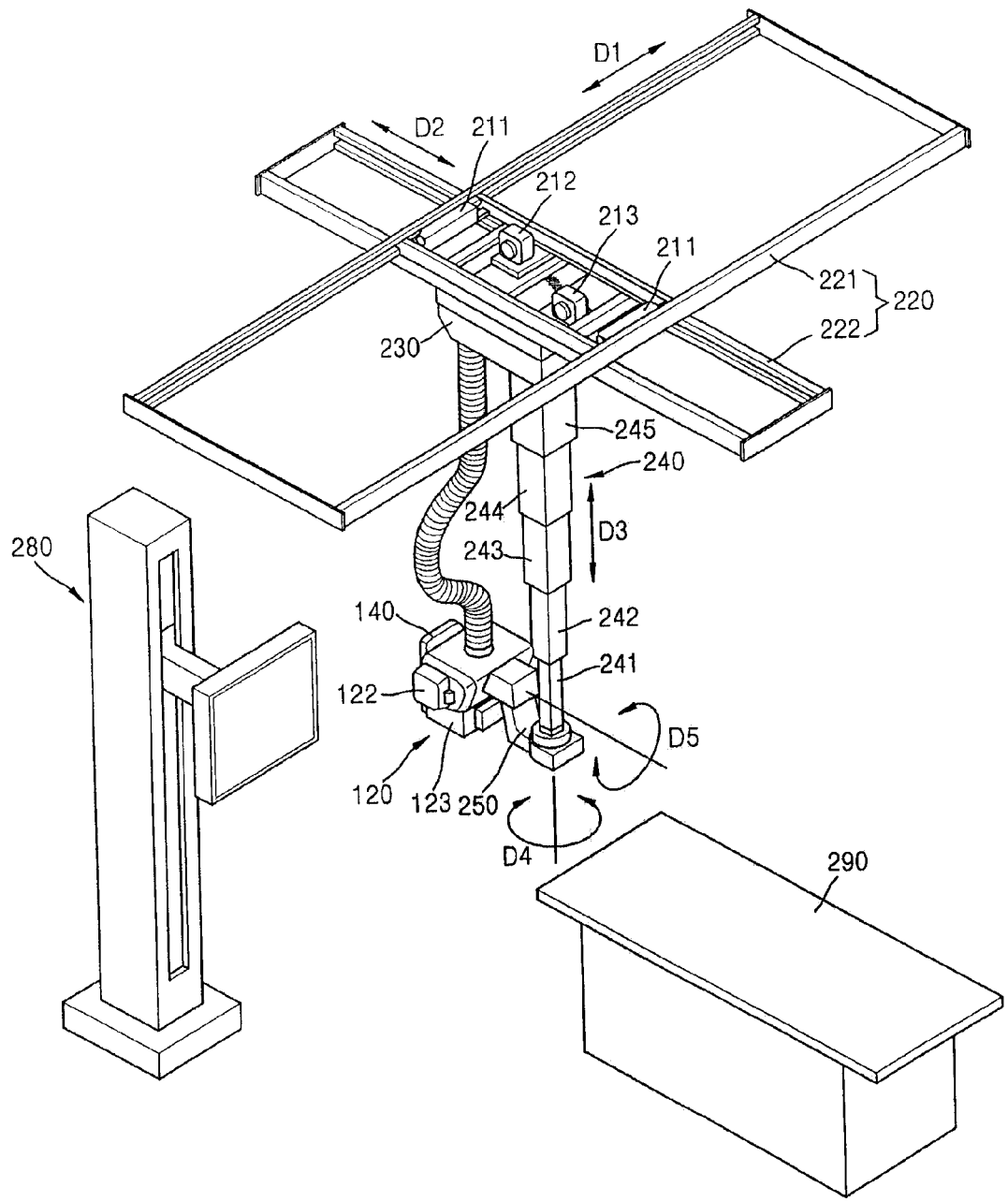
FIG. 3B is a diagram illustrating a fixed-type X-ray apparatus.

FIG. 3B is a diagram illustrating a fixed-type X-ray apparatus 200.

FIG. 3B is a perspective view illustrating the fixed-type X-ray apparatus 200. The fixed-type X-ray apparatus 200 of FIG. 3B may be an embodiment of the X-ray apparatus 100 of FIG. 1. Among elements included in the fixed-type X-ray apparatus 200 of FIG. 3B, the same elements as those of FIG. 1 are referred to by the same reference numerals as those of FIG. 1, and a repetitive description is not provided.

The fixed-type X-ray apparatus 200 includes a manipulation unit 140 for providing a user with an interface for manipulating the fixed-type X-ray apparatus 200, an X-ray irradiation unit 120 irradiating X-rays to an object 10, a detector 130 detecting the X-rays that have passed through the object 10, first through third motors 211, 212, and 213 providing a driving power to transport the X-ray irradiation unit 120, a guide rail 220, a moving carriage 230, and a post frame 240 formed to transport the X-ray irradiation unit 120 by using the driving power of the motors 211, 212, and 213.

The guide rail 220 includes a first guide rail 221 and a second guide rail 222 that are provided to form a predetermined angle with respect to each other. The first guide rail 221 and the second guide rail 222 may respectively extend in directions crossing each other.

The first guide rail 221 is provided on a ceiling of the examination room in which the fixed-type X-ray apparatus 200 is disposed.

The second guide rail 222 is located under the first guide rail 221, and is mounted onto the first guide rail 221 so as to slide along the first guide rail 221. A roller (not shown) that may move along the first guide rail 221 may be provided on the first guide rail 221. The second guide rail 222 is connected to the roller (not shown) to move along the first guide rail 221.

A first direction D1 is defined as a direction in which the first guide rail 221 is extended, and a second direction D2 is defined as a direction in which the second guide rail 222 is extended. Therefore, the first direction D1 and the second direction D2 cross each other, and may be parallel to the ceiling of the examination room.

The moving carriage 230 is disposed under the second guide rail 222 so as to move along the second guide rail 222. A roller (not shown) moving along the second guide rail 222 may be provided on the moving carriage 230.

Therefore, the moving carriage 230 may move in the first direction D1 with the second guide rail 222, and may move in the second direction D2 along the second guide rail 222.

The post frame 240 is fixed on the moving carriage 230 and located under the moving carriage 230. The post frame 240 may include a plurality of posts 241, 242, 243, 244, and 245.

The plurality of posts 241, 242, 243, 244, and 245 are connected to each other to be foldable, and thus, the post frame 240 may have a length that is adjustable in an up and down direction of the examination room in a state of being fixed to the moving carriage 230.

A third direction D3 is defined as a direction in which the length of the post frame 240 is increased or reduced. Therefore, the third direction D3 may cross the first direction D1 and the second direction D2.

The detector 130 detects X-rays passing through an object 10, and may be coupled to a table-type receptor 290 or a stand-type receptor 280.

A rotating joint 250 is disposed between the X-ray irradiation unit 120 and the post frame 240. The rotating joint 250 allows the X-ray irradiation unit 120 to be coupled to the post frame 240, and supports a load applied to the X-ray irradiation unit 120.

The X-ray irradiation unit 120 connected to the rotating joint 250 may rotate on a plane that is perpendicular to the third direction D3. Here, a rotating direction of the X-ray irradiation unit 120 may be defined as a fourth direction D4.

Also, the X-ray irradiation unit 120 may be configured to be rotatable on a plane perpendicular to the ceiling of the examination room. Therefore, the X-ray irradiation unit 120 may rotate in a fifth direction D5 that is a rotating direction based on an axis that is in parallel with the second direction D2, with respect to the rotating joint 250.

The motors 211, 212, and 213 may be provided to move the X-ray irradiation unit 120 in the first through third directions D1, D2, and D3. The motors 211, 212, and 213 may be electrically driven, and the motors 211, 212, and 213 may respectively include an encoder.

The motors 211, 212, and 213 may be disposed on various positions in consideration of design convenience. For example, the first motor 211 moving the second guide rail 222 in the first direction D1 may be disposed around the first guide rail 221, the second motor 212 for moving the moving carriage 230 in the second direction D2 may be disposed around the second guide rail 222, and the third motor 213 increasing or reducing the length of the post frame 240 in the third direction D3 may be disposed in the moving carriage 230. In another example, the first through third motors 211, 212, and 213 may be connected to a driving power transfer unit (not shown) so as to linearly move the X-ray irradiation unit 120 in the first through third directions D1, D2, and D3. The driving power transfer unit (not shown) may be a belt and a pulley, a chain and a sprocket, or a shaft that are generally used.

As another example, motors may be disposed between the rotating joint 250 and the post frame 240 and between the rotating joint 250 and the X-ray irradiation unit 120 in order to rotate the X-ray irradiation unit 120 in the fourth direction D4 and the fifth direction D5.

The manipulation unit 140 may be disposed at one side of the X-ray irradiation unit 120.

Although FIG. 3B shows the fixed-type X-ray apparatus 200 connected to the ceiling of the examination room, the fixed-type X-ray apparatus 200 of FIG. 3B is an example for convenience of comprehension. That is, the X-ray apparatus according to the embodiments of the present invention may be an X-ray apparatus having various structures, for example, a C-arm-type X-ray apparatus and an angiography X-ray apparatus, without departing from the spirit and scope of the invention which are obvious to those skilled in the art.

Figure 3C:
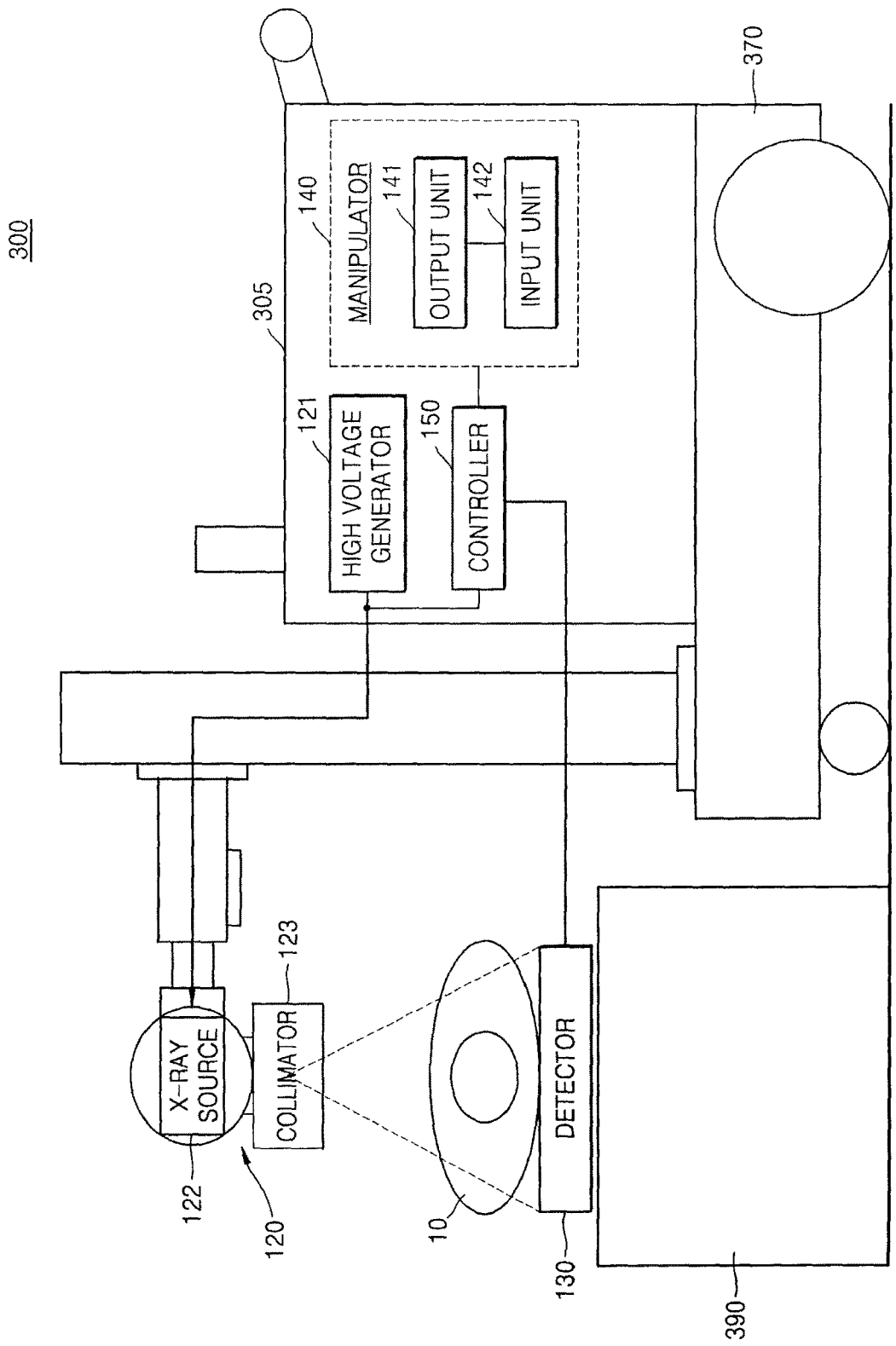
FIG. 3C is a diagram illustrating a mobile X-ray apparatus.

FIG. 3C is a diagram illustrating a mobile X-ray apparatus 300.

FIG. 3C is a diagram showing a configuration of a mobile X-ray apparatus 300 capable of performing an X-ray imaging operation regardless of a place where the imaging operation is performed, according to an embodiment of the present invention. The mobile X-ray apparatus 300 of FIG. 3C may be an embodiment of the X-ray apparatus 100 of FIG. 1. Among elements included in the mobile X-ray apparatus 300 of FIG. 3C, the same elements as those of FIG. 1 are referred to by the same reference numerals as those of FIG. 1, and a repetitive description is not provided.

The mobile X-ray apparatus 300 shown in FIG. 3C includes: a transport unit 370 including a wheel for transporting the mobile X-ray apparatus 300, a main unit 305 including a manipulation unit 140 providing an interface for manipulating the mobile X-ray apparatus 300, a high voltage generator 121 generating a high voltage applied to an X-ray source 122, and a control unit 150 controlling an overall operation of the mobile X-ray apparatus 300; an X-ray irradiation unit 120 including the X-ray source 122 generating the X-rays and a collimator 123 for guiding a path of the X-rays generated and emitted from the X-ray source 122 to adjust an irradiation region of the X-rays; and a detector 130 detecting the X-rays irradiated from the X-ray irradiation unit 120 and transmitted through an object 10.

In FIG. 3C, the detector 130 is illustrated as a table type receptor 390, but it is obvious that the detector 130 may be implemented as a stand type receptor.

In FIG. 3C, the manipulation unit 140 is illustrated as being included in the main unit 305, but the present embodiment is not limited thereto. For example, as illustrated in FIG. 3A, the manipulation unit 140 of the mobile X-ray apparatus 300 may be provided at one side of the X-ray irradiation unit 120.

A radiation detector according to an exemplary embodiment is an apparatus for sensing radiation, and senses an incident radiation photon in a direct type. Therefore, the radiation detector according to an exemplary embodiment may be applied to all electronic devices that sense a radiation photon.

In detail, the radiation detector according to an exemplary embodiment may correspond to the X-ray detecting unit 178 described above with reference to FIGS. 1A and 1B, and may be included in the CT system 20 described above with reference to FIGS. 1A and 1B. In detail, the radiation detector according to an exemplary embodiment may be a radiation detector that is used to generate a tomography image. In detail, the radiation detector according to an exemplary embodiment may be a radiation detector that is used to generate a CT image. In detail, the radiation detector according to an exemplary embodiment may sense the radiation that is emitted from the X-ray generating unit 176, which includes an X-ray source 122 that is attached to the gantry 172 of FIGS. 1A and 1B and rotates, and has passed through the object.

Moreover, the radiation detector according to an exemplary embodiment may correspond to the detector 130 described above with reference to FIGS. 3A and 3B, and may be included in the X-ray system 1000 or the X-ray apparatuses 100, 200 and 300 described above with reference to FIGS. 3A to 3C. In detail, the radiation detector according to an exemplary embodiment may be a radiation detector that is used to generate an X-ray image. In detail, the radiation detector according to an exemplary embodiment may sense the radiation that is emitted from the X-ray irradiation unit 120, which includes an X-ray source 122 that is attached to a moving apparatus and is adjusted in position, and has passed through the object 10. Here, the moving apparatus to which the X-ray source 122 is attached may include at least one selected from the guide rail 220, the moving carriage 230, and the post frame 240 which have been described above with reference to FIG. 3B. Also, the moving apparatus may include the transport unit 370 described above with reference to FIG. 3C.

The radiation detector according to an exemplary embodiment will now be described in detail with reference to FIGS. 4 to 9.

Figure 4:
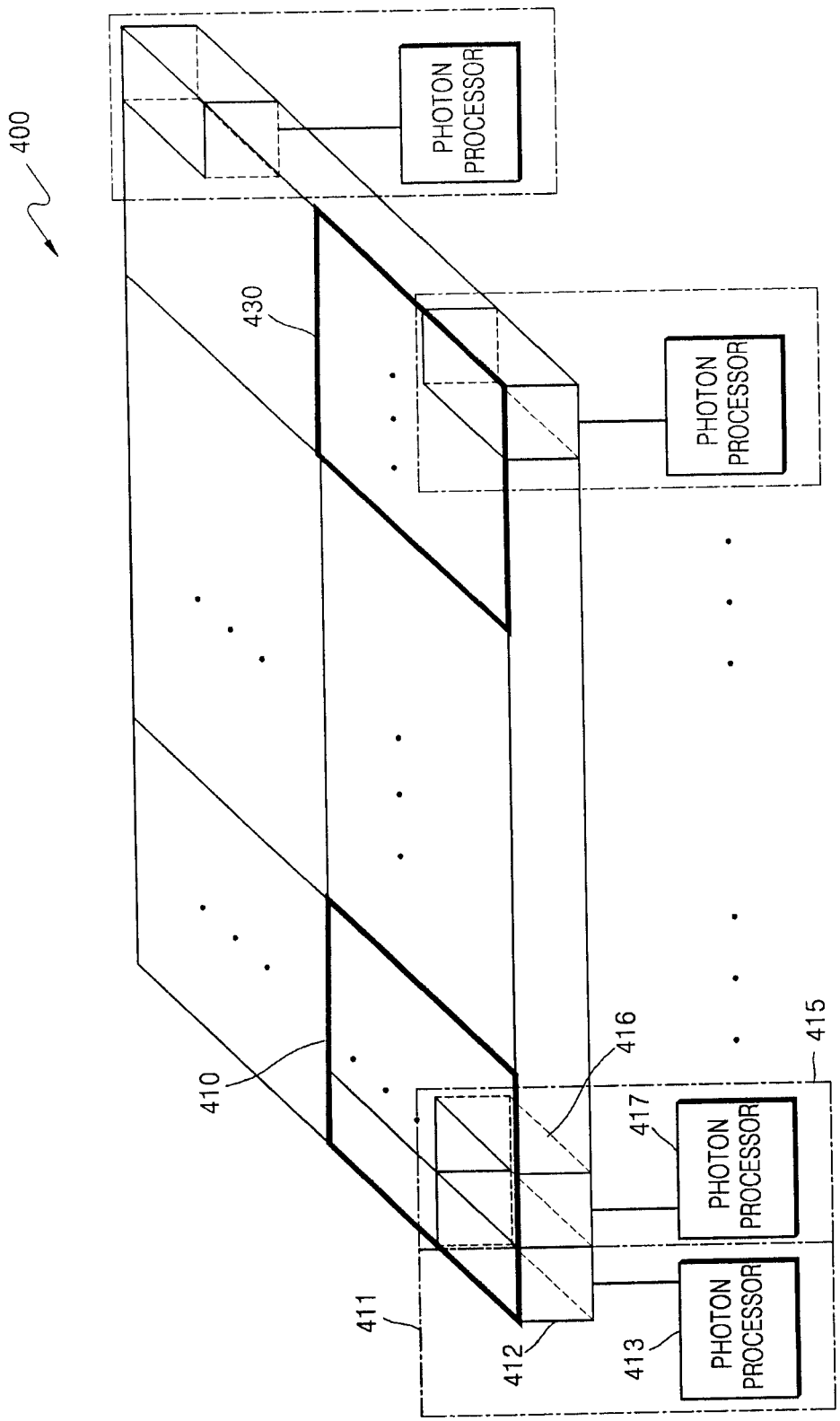
FIG. 4 is a diagram illustrating a radiation detector according to an embodiment of the present invention.

FIG. 4 is a diagram illustrating a radiation detector 400. The radiation detector 400 is a photon counting detector that converts incident radiation into an electric charge in a direct method to detect the radiation, after having been passed through the object 10. In detail, the radiation detector 400 is a photon counting detector that converts an incident radiation photon into an electrical signal, and counts the number of converted electrical signals corresponding to the photons.

Referring to FIG. 4, the radiation detector 400 according to an embodiment of the present invention includes a plurality of pixels 410 and 430 that detect radiation. Each of the plurality of pixels 410 and 430 includes a plurality of sub-pixels 411 and 415. Hereinafter, one pixel includes a number m of sub-pixels, and the sub-pixel 411 being one of the sub-pixels of the pixel 410 may be a counting pixel and will be described as an example.

Specifically, the radiation detector 400 may be a radiation detector used to generate a CT image, and may correspond to the X-ray detecting unit 178 of FIGS. 1A and 1B.

The plurality of pixels 410 and 430, as illustrated, may have a tetrahedral structure which is arranged in a lattice form and the pixels may have the same shape and/or size.

The sub-pixel 411 includes a radiation absorption layer 412, and a photon processor 413.

Here, counting incident photons is performed in units of a sub-pixel 411, and thus, the sub-pixel 411 may be referred to as a counting pixel. Hereinafter, a sub-pixel which is a partial pixel included in the pixel 410 is referred to as a counting pixel. Also, one pixel value of an image which is restored based on the number of photons counted in at least one counting pixel may be determined, and thus, a counting pixel group including at least one counting pixel may be referred to as an image pixel. For example, when one pixel value of an image is acquired based on the number of photons counted in a plurality of counting pixels 411 and 415 included in the pixel 410, an image pixel becomes the pixel 410. As another example, when one pixel value of an image is acquired based on the number of photons counted in four adjacent counting pixels, an image pixel may become a counting pixel group including four counting pixels.

In detail, the radiation detector 400 includes at least one counting pixel 411, and includes a plurality of image pixels for restoring an image. The counting pixel 411 includes the radiation absorption layer 412, which converts an incident photon into an electrical signal, and a photon processor 413 that counts the number of photons, based on the electrical signal transferred from the radiation absorption layer 412. Here, the number of image pixels included in the radiation detector 400 is smaller than the number of the counting pixels 411. Also, a size of each of the image pixels included in the radiation detector 400 is greater than a size of a counting pixel.

In detail, the counting pixel 411 counts the number of photons which are smaller than the number of photons incident on an image pixel.

In detail, an image pixel corresponds to one pixel value constituting an image, and one pixel value in an image is calculated based on the total number of photons counted in one image pixel. In detail, an image pixel may include a plurality of counting pixels, and one pixel value in an image is calculated based on the total number of photons counted in a counting pixel group including a plurality of counting pixels. When a plurality of counting pixels included in the pixel 410 constitute one counting pixel group, the pixel 410 may become one image pixel. Also, when the plurality of counting pixels included in the pixel 410 constitute a plurality of counting pixel groups, the pixel 410 corresponds to one image pixel of one counting pixel group, and thus may include a plurality of image pixels.

Moreover, in the radiation detector 400 including a plurality of the pixels 410 that sense radiation, the pixel 410 includes a plurality of counting pixels 411 and 415 that sense radiation for restoring an image. Here, the counting pixel 411 includes the radiation absorption layer 412, which converts an incident photon into an electrical signal, and a photon processor 413 that counts the number of photons, based on the electrical signal.

The radiation absorption layer 412 may be arranged at or on any other surface than the surface oriented towards the X-ray source 122, such as a side or a back surface. In the depicted embodiment, the radiation absorption layer 412 may be constituted by the entire thickness of the layer depicted in FIG. 4 or may be arranged on a side surface of the sub-pixel 411.

The radiation absorption layer 412 may convert an incident X-ray photon into an electrical signal. The radiation absorption layer 412 may transfer electrical signal to the photon processor 413.

Moreover, the radiation absorption layer 412 may be formed on at least one portion of a surface facing an X-ray source 122. In detail, the radiation absorption layer 412 may be formed on a front surface of the radiation detector 400 which is the surface facing the X-ray source 122, sides of the surface facing the X-ray source 122, or at least one portion of a rear surface of the radiation detector 400 on which X-rays from the X-ray source 122 are likely to be incident due to scattering. In FIG. 4, a case in which the radiation absorption layer 412 is formed on the front surface of the radiation detector 400 facing the X-ray source 122 to have a uniform thickness is illustrated as an example.

In detail, the radiation absorption layer 412 may directly convert radiation photon into an electrical signal, and may be formed from cadmium telluride (CdTe). CdTe is a semiconductor material. Potentially, the photon processor 413 and memory can be formed in an underlying semi-conductor layer as indicated at 520 in FIG. 5A, even though the exemplary material CdTe is in itself less suitable to integrate any semi-conductor components therein. The underlying layer or rear part 520 may be formed of other semi-conductor material for the same purpose also. Regardless of whether the underlying layer or rear part is made from CdTe too, or from an alternative semi-conductor material, a very compact configuration can be obtained with integrated semi-conductor components.

The photon processor 413 counts absorbed photons. In detail, the photon processor 413 counts the number of photons based on the electrical signal generated by the radiation absorption layer 412 according to a direct method that directly converts an incident photon into an electric charge to detect the photon.

In detail, the photon processor 413 compares energy of the absorbed photons with a reference value, and counts the number of photons having energy equal to or greater than the reference value.

The photon processor 413 may include a counting memory (not shown) that stores the number of counted photons. In detail, the photon processor 413 included in the counting pixel 411 may count and store the number of photons smaller than the number of photons which are incident on an image pixel for a certain time.

The memory (not shown) stores a value obtained through the counting by the photon processor 413. The memory (not shown) has a storage capacity of about n/m value when the pixel 410 absorbs about number n of photons during a certain, predetermined period of time, and wherein m denotes the number of sub-pixels.

Referring to FIG. 4, the sub-pixel 411 includes the photon processor 413 and the memory (not shown), and the sub-pixel 415 includes a photon processor 417 and a memory (not shown).

The photon processor 413, as illustrated, is included in each counting pixel 411, and allows a photon counting operation to be separately performed for each counting pixel 411.

A structure of each pixel and a structure of each counting pixel will be described in detail with reference to FIGS. 5 to 7.

Figure 5A:
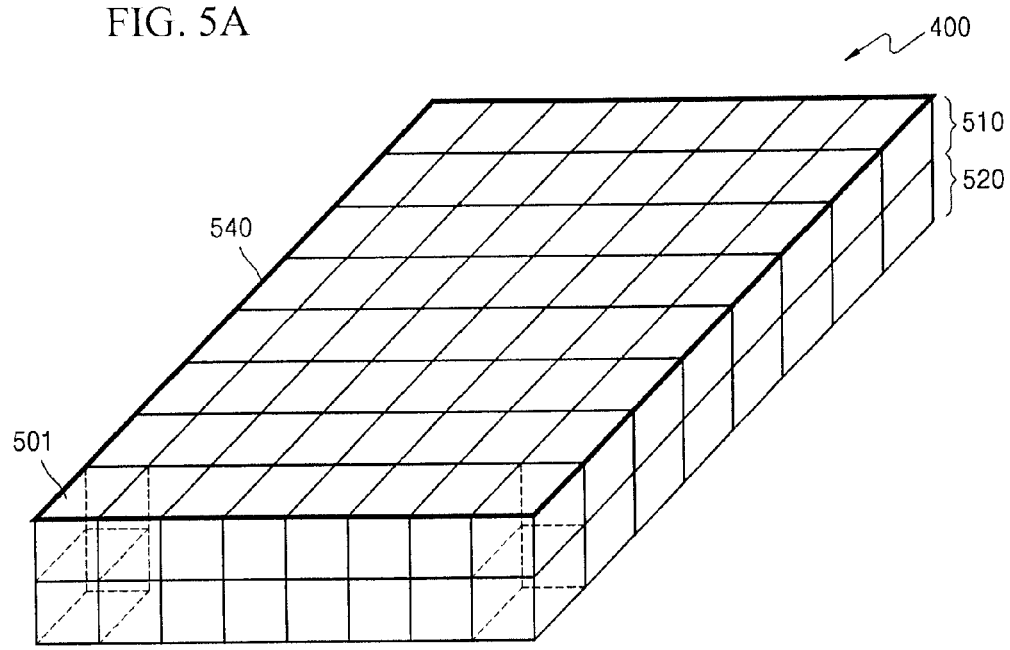
FIGS. 5A and 5B are diagrams for describing a plurality of pixels of FIG. 4.
Figure 5B:
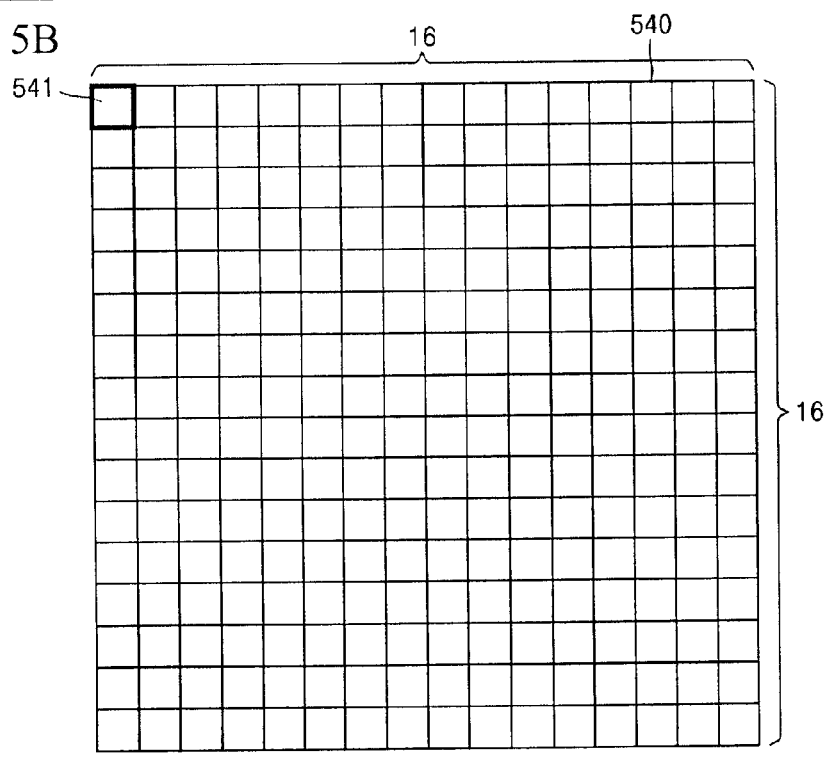

FIGS. 5A and 5B are diagrams for describing a plurality of pixels of FIG. 4.

Referring to FIG. 5A, the radiation detector 400 includes a plurality of pixels that are arranged in a lattice form. A reference numeral 501 indicates a pixel. In FIG. 5B, in a front view, a case in which 256 pixels (16*16 pixels) are included in the radiation detector 400 is illustrated as an example. In FIG. 5A a perspective view is depicted of a portion of this radiation detector 400.

Referring to FIGS. 4 and 5A, the radiation absorption layer 412 and a radiation absorption layer 416 may be disposed in or at a front part 510 of the radiation detector 400. The photon processor 413, a photon processor 417, and the memories (not shown) may be disposed at, on, behind or at a side of a rear part 520 of the radiation detector 400. The front part 510 may include the radiation absorption layers 412 and 416, in this embodiment. Relative expression "front" and "rear" are used herein with respect to a direction from which X-ray is incident on the radiation detector 400. As indicated above, the rear part 520 may be formed from semi-conductor material, and the photon processor 413 and 417 and memory of each sub-pixel 411 may be realized therein, to provide a very compact configuration, resembling or forming a sandwich structure.

Specifically, radiation passing through an object 10 is incident onto the front surface 540 of the radiation detector 400, wherein the radiation absorption layers 412 and 416 disposed in or at the front part 510 absorb the incident radiation and transfer electrical signals to the respective photon processors 413 and 417 which are respectively connected to the radiation absorption layers 412 and 416. In detail, the radiation absorption layers 412 and 416 convert a photon (incident radiation) into an electrical signal, and transfer the converted electrical signal to the photon processors 413 and 417.

A front surface of one pixel 541 may have a size of 1 mm*1 mm=1 mm$^2$. In detail, a length of one side edge of the one pixel 541 delimiting the circumference of one pixel 541 in of FIG. 5B may be about 0.9 mm to about 1.1 mm.

Figure 6A:
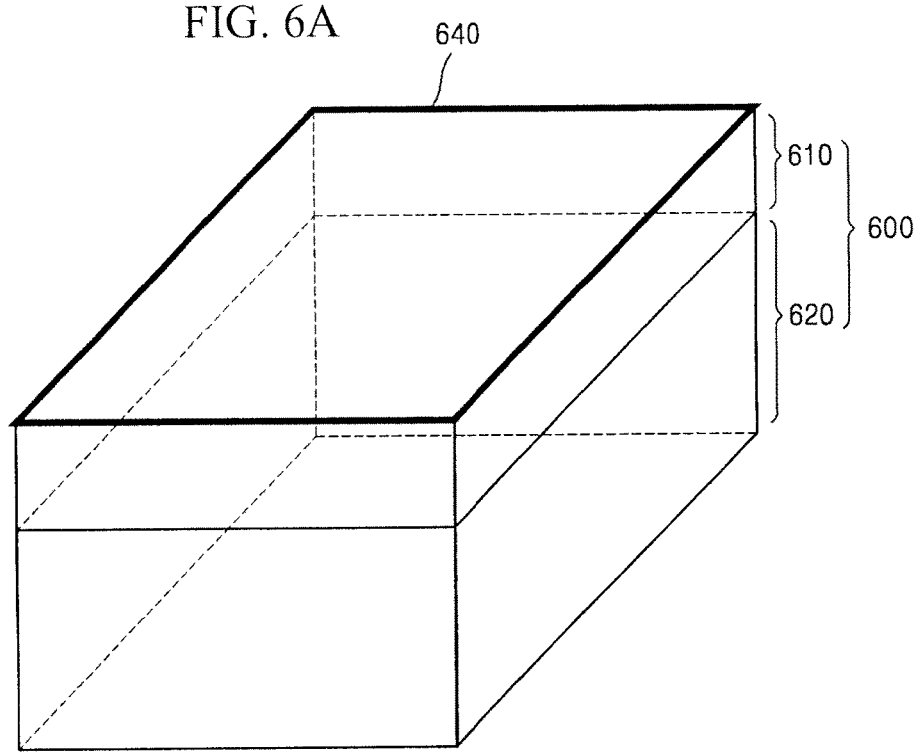
FIGS. 6A, 6B, and 6C are diagrams for describing a counting pixel of FIG. 4.
Figure 6B:
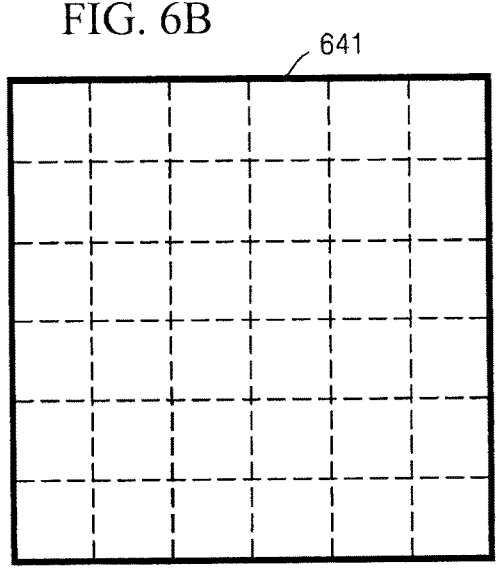
Figure 6C:
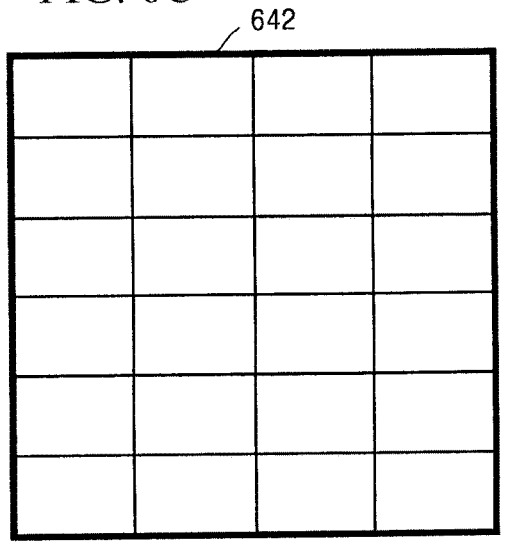

FIGS. 6A, 6B, and 6C are diagrams for describing a sub-pixel 411 of FIG. 4.

Referring to FIG. 6A, one pixel 600 may include a plurality of sub-pixels. For example, the one pixel 600 in front view 642 of FIG. 6C may include 24 pixels (4*6 pixels), and the one pixel 600 in front view 641 of FIG. 6B may include 36 pixels (6*6 pixels). Alternatively, the pixel 600 may include (not shown) 16 pixels (4*4 pixels); 25 pixels (5*5 pixels); 36 pixels (6*6 pixels); 35 pixels (7*5 pixels), and assemblies of sub-pixels may be rectangular, as described and shown, or alternatively be square, honeycomb-shaped, triangular, diamond-shaped or cross-shaped (for instance comprising 5, 20 or 45, etc. pixels), any combination(s) of such and/or other shapes or have any other suitable front vies shape, where a consideration is that sub-pixels should be closely adjoining or neighboring to cover the entire surface of the pixels to which the sub-pixels belong and which pixels are constituted by these sub-pixels.

The radiation detector included in the CT system may absorb a certain number of photons when imaging an object under a certain imaging condition. The number of photons, which are absorbed and counted by one pixel having a unit area of about 1 mm$^2$, may be determined according to the following spectrum modeling.

In imaging conditions for a photon counting detector included in a high-class or high specification CT system, a tube voltage may be set to about 120 kVp, a tube current may be set to a minimum of 200 mA or more, and an aluminum equivalent thickness corresponding to a filter condition may be set to about 5.6 mm.

Under the imaging conditions, the number of photons absorbed and counted by the one pixel 600 may be calculated according to X-ray spectrum modeling based on a tungsten anode spectral model using interpolating polynomials (TASMIP).

Specifically, the number of photons which are absorbed by one pixel per second may be about two hundred million to about five hundred million. Here, the one pixel may have a unit area of 1 mm$^2$.

For example, the spectrum modeling may be designed as follows.

| Item | Modeled Value | Unit |
| --- | --- | --- |
| Mean Photon Energy | 60.605 | [keV] |
| 1st Half Value Layer | 6.886 | [mm Al] |
| Exposure | 7.739 | [mR/mAs] @ 1.0 [m] |
| Air Kerma | 67.799 | [uGy/mAs] @ 1.0 [m] |
| Fluence | 2,004,955 | [photons/mm$^2$/mAs] @ 1.0 [m] |

In the spectrum modeling, the mean photon energy is about 60.605 keV (kilo electron volts), and the 1st half value layer is 6.886 mm Al. The exposure is about 7,730 mR/mAs when the measurement is performed at a distance of about 1 m, and the air kerma is about 67.799 uGy/mAs when the measurement is performed at a distance of about 1 m. Under the modeling conditions, the fluence which passes through a unit area of 1 mm$^2$ and is incident is 2,004,955 [photons/mm$^2$/mAs] when the measurement is performed at a distance of about 1 m.

According to the spectrum modeling, the number of photons which are generated when X-rays of about 1 mA are emitted is about 2,004,955 photons/mm$^2$/mAs, namely, about 2 mega photons/mm$^2$/mAs. Hereinafter, mega (M) is used as a unit of million.

In case of a detector having a dose of about 200 mA, the number of photons incident onto a unit area of about 1 mm$^2$ may be about 200*2,004,955 photons/mm$^2$/s, namely, about 400 M photons/mm$^2$/s. Also, when the detector operates at a dose of about 100 mA, i.e. when a dose of radiation is reduced by about 50%, the number of photons incident onto a unit area of about 1 mm$^2$ may be about 100*2,004,955 photons/mm$^2$s, namely, about 200 M photons/mm$^2$/s.

Therefore, the one pixel 600 having a unit area of about 1 mm$^2$ may absorb and count 200 M or more photons per second. To achieve a desired resolution, a minimum value of for instance 200 M photons/mm$^2$ may even be required, but accumulating a count value of 200 M photons per 1 mm$^2$ pixel size may take a longer time than available in the related art radiation detectors, which is detrimental especially but not only in CT scanners, where speed of successive image registrations is of paramount importance. In any case, a requirement on radiation detectors of being able to register 200 M photons per mm$^2$ per second has to date eluded the skilled persons in the present technical field, which will be explained in more detail herein below.

Although a minimum of 200 M photons/mm$^2$ per second is indicated here as a current requirement, the value thereof may vary in time, and it is noted here that the present invention according to the present disclosure is capable of complying with higher and even much higher minimum requirements than the above mentioned 200 M photons per mm$_2$ per second.

Also, one counting pixel of 25 counting pixels in the pixel (when the value of m is 25) may absorb and count about 8 M (200 M/25) or more photons per second. Consequently, the pixel as a whole is better capable of absorbing and counting the impinging dose of 200 M photons than the any embodiment with only a whole pixel, which is then required to absorb and count the full amount of the 200 M photons, as will be described below more fully.

Referring to FIG. 6B, pixel 600 shown in front view 641 may include 36 counting pixels (6*6 counting pixels). That is, a front surface 640 of the pixel 600 may be the front view 641 in FIG. 6B. As described above, when the pixel 600 absorbs and counts about 200 M photons per second and includes 36 counting pixels, one counting pixel may absorb and count 5.56 M photons (200/36 M photons) per second.

Referring to FIG. 6C, pixel 600 shown in front view 642 may include 24 counting pixels (6*4 counting pixels). That is, a front surface 640 of the pixel 600 may be the front view 642 in FIG. 6C. As described above, when the pixel 600 absorbs and counts about 200 M photons per second and includes 24 counting pixels, one counting pixel may absorb and count 8.336 M photons (200/24 M photons) per second. Moreover, the pixel 600 may include 25 counting pixels (5*5 counting pixels). As described above, when the pixel 600 absorbs and counts about 200 M photons per second and includes 25 counting pixels, one counting pixel may absorb and count 8 M photons (200/25 M photons) per second.

As in the above-described embodiment, the number of photons counted for a certain time may be set based on a detailed product specification (for example, an X-ray apparatus, a tomography imaging apparatus, or the like) to which the radiation detector is applied, and the number and size of counting pixels included in one pixel may be adjusted based on the set number of photons. For example, a size of the counting memory included in the photon processor may be adjusted based on the set number of photons. Additionally, it is noted here that in FIG. 6A, the pixel 600 is also shown to have a front part 610 and a rear part 620, where the front surface 640 is on the front part 610, relative to a direction from incident which incident radiation.

Figure 7A:
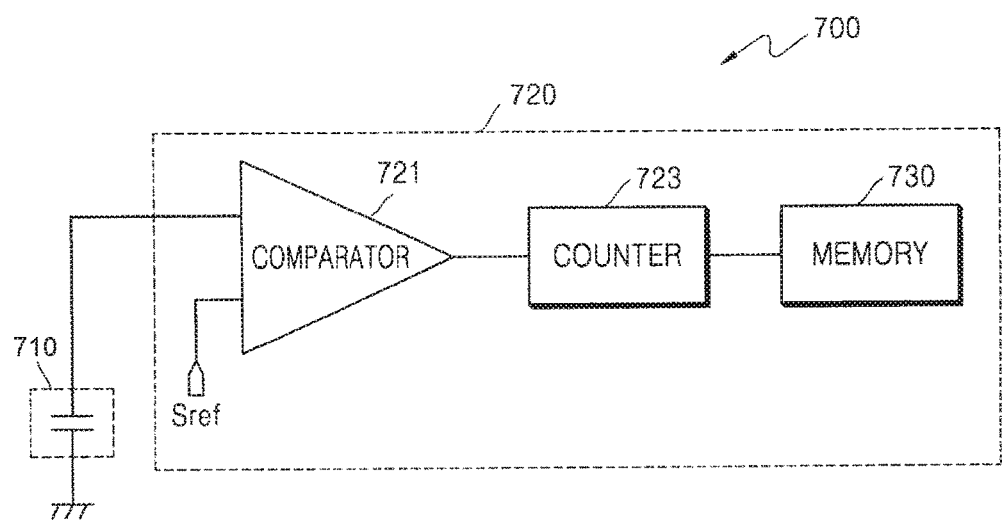
FIG. 7A is another diagram for describing the counting pixel of FIG. 4.
Figure 7B:
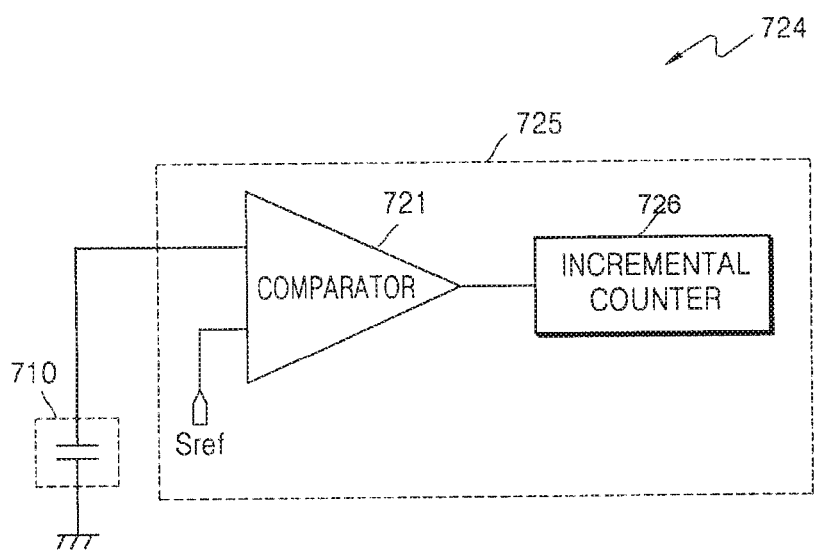
FIG. 7B is another diagram for describing the counting pixel of FIG. 4.

FIGS. 7A and 7B are diagrams for describing a counting pixel 411 of FIG. 4.

Referring to FIG. 7A, in the radiation detector, a counting pixel 700 includes a radiation absorption layer 710, a photon processor 720, and a memory 730. The radiation absorption layer 710 is the same or at least comparable with the radiation absorption layer 412 or 416 in FIG. 4.

The radiation absorption layer 710 converts an incident X-ray photon into an electrical signal. The radiation absorption layer 710 may be disposed at a front part of the counting pixel 700, and may include a capacitor formed by or from CdTe. The radiation absorption layer 710 may absorb X-ray photons, and may be charged with an electrical signal obtained by converting each of the X-ray photons. The radiation absorption layer 710 may transfer the charged electrical signal to the photon processor 720. Here, the electrical signal obtained through conversion by the radiation absorption layer 710 may be a voltage signal.

The photon processor 720 may include a comparator 721 and a counter 723.

The comparator 721 compares the electrical signal with a reference value to determine whether the electrical signal exceeds the reference value. In detail, when the electrical signal is a voltage signal, the comparator 721 compares the electrical signal corresponding to the photon with a predetermined reference voltage Sref. When the electrical signal is greater than the reference voltage Sref as a comparison result, the comparator 721 outputs a signal, which is to be accumulated and counted by the counter 723, to the counter 723.

Here, the reference voltage Sref is a value corresponding to energy of the photon, and may be changed according to an X-ray source 122. For example, a value that enables determination of whether the electrical signal input from the comparator 721 is generated by converting the photon may be set as the reference value Sref.

The counter 723 counts the number of photons according to an output signal of the comparator 721.

For example, when the comparator 721 is biased to a +Vh voltage and a −Vh voltage, the comparator 721 may output the +Vh voltage as a logic high level signal, and output the −Vh voltage as a logic low level signal. When a level of the electrical signal corresponding to the photon is higher than that of the reference voltage Sref, the comparator 721 may output the +Vh voltage corresponding to the logic high level, and when the +Vh voltage is input to the counter 723, the counter 723 may increment a count value of the number of incident photons by +1 and thus count the number of photons. On the other hand, when a level of the electrical signal corresponding to the photon is lower than that of the reference voltage Sref, the comparator 721 may output the −Vh voltage, and when the −Vh voltage is input to the counter 723, the counter 723 may continue to accumulate the count value of number of photons, without incrementing the value of the number of photons for an electrical signal from the radiation absorption layer 710 to the comparator 721 of the photon processor 720, that has resulted in the logic low level, i.e., for which the comparator 721 has distinguished that the electrical signal from the radiation absorption layer 710 does not correspond with impingement of a photon thereon.

The memory 730 stores the number of photons counted by the counter 723. In detail, when one counting pixel 700 absorbs n number of photons for a certain time, the memory 730 needs to have a storage capacity of n/m value. For example, when the counting pixel 700 absorbs and counts about 200 M or more photons per second and includes 25 counting pixels, the memory 730 stores the number of bits corresponding to about 8 M so as to store 8 M or more photons (200/25 M photons) per second. A storage capacity of the memory 730 may be set based on the number of photons which is counted by one counting pixel for a certain time.

Moreover, FIG. 7A, a case in which the memory 730 is included in the photon processor 720 is illustrated as an example, but the memory 730 may be provided independently from the photon processor 720.

In FIG. 7B, an alternative embodiment for the configuration of FIG. 7A is exhibited. In the radiation detector according to FIG. 7B a counting pixel 724 includes a radiation absorption layer 710, a comparator 721 like the one in FIG. 7A and an incremental counter 726 forming an embodiment of the photon processor 725. The photon processor 725 may include also the comparator 721, as indicated by the dotted line in FIG. 7B, or be formed by only the incremental counter 726. An operating system may periodically read out values accrued in the incremental counter 726 and reset the value accrued therein to zero, whereafter a new period of counting impinging photons can start. Thereby the need for a separate counter and memory as in the embodiment of FIG. 7A can be avoided in a simple and elegant manner. Especially, a separate memory can be omitted.

Also, the incremental counter 726 may be referred to as a counting memory 726. In detail, the counting memory 726 counts and stores the number of photons according to an output signals of the comparator 721. And, a storage capacity of the counting memory 726 may be set based on the number of photons which is counted by one counting pixel for a certain time.

The memory capacity of the memory 730 in FIG. 7A or count value capacity of an incremental counter 726 in FIG. 7B may vary or be set or designed, depending on numbers m of counting pixels per pixel and the amount of photons, expected to impinge on the radiation absorption layer 710 during a measurement time period, which may be the "certain time" referred to elsewhere in the present disclosure. Any memory (separate or integrated) or incremental counter 726 may be read out in real time. Herein below, the expression of memory capacity is also employed to indicate a maximum count value of an incremental counter 726 in or of the embodiment of FIG. 7B.

The impression may be obtained from the representation of FIGS. 7A and 7B that the comparator, counter and—if present—the memory are arranged close to the counting pixels or at least form part of the detector unit, but in fact the counter or other form of photon processor, the comparator (if present) and memory (if present) can or will be arranged in or at the DAS 186 of FIG. 1B.

Assuming that a radiation detector is designed to have 25 counting pixels 700 per pixel, and in use will be subjected to no more than 500 M photons per the certain time, then the memory capacity for a count value of 500 M/25=20 M for each memory of every counting pixel is considered sufficient, also for application at lower levels of photon impingement and consequently lower X-ray tube output. It is possible, within the framework of the present disclosure and the appended claims, to set the select a memory size in correspondence with a predetermined, given number m of counting pixels. e.g. 25 counting pixels, per pixel in view of a maximum incident radiation, e.g. 500 M photons. Under circumstances of 200 M photons, the memory capacity would in any case suffice of (500 M/25=) 16 M where under such circumstances a capacity of (200 M/25=) 8 M would be sufficient. Further, a design trade-off between required maximum memory capacity of memories 730 or the maximum count value of the incremental counter 726, maximum incident radiation n and the number m of counting pixels, a number m of sub-pixels can be altered, for example to allow a higher or lower required maximum memory capacity. For instance, by employing a design having 36 counting pixels per pixel instead of 25 counting pixels per pixel, at a maximum incident radiation of 500 M photons, the maximum required memory capacity can be reduced to a maximum count value of (500 M/36=) 13.89 M. However, as explained below, the counting pixel design of pixels allows combinations of counting pixels to be created to redefine, in use, the size or shape or other parameter of pixels, and thus create new borders or boundaries of pixels depending on the circumstances of use, in particular the numbers of impinging photons per time unit. This allows even for the functionality, that a number of counting pixels per pixel may be reduced, if required count values are acquired too quickly, or increased, if the necessary count values are obtained not quickly enough. Similarly, the exposure time or certain time or time period in which the incident radiation is allowed to impinge on the radiation detector can be reduced, as a consequence of a higher counting speed, as will be elaborated below. For example, if more incident radiation can be detected reliably, a shorter exposure time (also referred as the certain time in other parts of the present disclosure) may be reduced and therewith the maximum incident radiation in the certain time will be reduced, to allow the memories 730 to have a lower required capacity. In more detail, if the certain time is reduced from 1 sec. to for example a half of a second, the maximum incident radiation is halved to 250 M photons in half of a second. The required maximum memory capacity for each memory of every counting pixel in case of a configuration having a number 25 of counting pixels can then be lowered to hold a count value of (250 M/25=) 10 M.

With respect to the latter aspect of lowering the certain time or period or exposure time, it is noted that each of the number m of counting pixels per pixels accrues its own count value in memory 730 or in the incremental counter 726, or otherwise, per counting pixel. In a prior configuration without separate counting per counting pixel, when two or more photons impinge practically simultaneously on front surface 640 of the pixel 600 in FIG. 6A, for instance at a considerable distance between these impacts within the surface of the 1 mm$^2$ size pixel, there is a risk that the multiple and practically simultaneously impinging photons result in adding a single count value 1, whereas the count value in the memory of an entire pixel should be increased by the same number as the number of the practically simultaneously impinging photons. After all, in such a case the electrical signal from the photon absorption layer will be momentarily higher than the reference value, above which the comparator outputs a logical high level, but does not indicate that this is caused by multiple and practically simultaneously impinging photons. Consequently, a certain time or exposure time is needed to obtain sufficient data to reconstruct an image with sufficient detail and/or in a desired resolution, which may often be very much longer than a time in which 200 M pixels actually impinge on the 1 mm$^2$ sized pixel of the prior configurations.

As a novel feature to decrease a required certain time or exposure time, it is possible to enhance the assembly of the radiation absorption layer, the comparator and the counter, to be able to distinguish more quickly between practically simultaneously impinging photon. However, such an approach may result in considerable and heavy design requirements on the radiation absorption layer, the comparator and the counter of prior configurations having 1 mm$^2$ sized pixels, which requirement of faster distinguishing between photons may be difficult to meet, although it is by no means excluded from the present disclosure.

However, in the above described embodiments, the front surface 640 of the pixel is divided into the areas of a number m of counting pixels, where each of the counting pixels of the pixels counts photons impinging on respective counting pixels, and holds or stores the count values of impinged photons in the respective memories or incremental counter thereof. Since practically simultaneously impinging photons are not likely to impinge on the surface 640 of pixel 600 at exactly the same location, but are more likely to impinge on different counting pixels of the pixels, distinct photons that impinge practically simultaneously on different counting pixels of each pixel will be separately counted, contributing to the speed and total required time at which sufficient data is acquired to construct images in sufficient detail and/or resolution. Consequently, the total require certain time or exposure time may be reduced and/or the required minimum count speed is achieved, and as a consequence the maximum required capacity for count values in the memories of the separate counting pixels may also be reduced. Consequently, a higher speed count radiation detector can be provided.

Figure 8A:
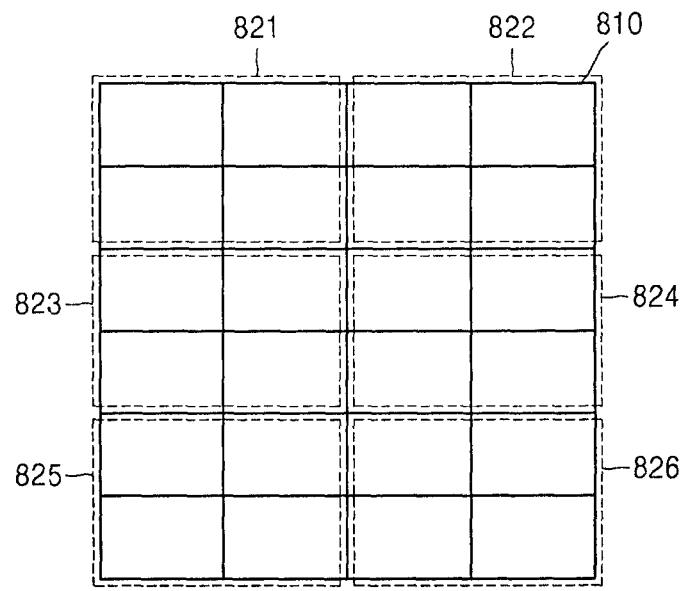
FIGS. 8A and 8B are diagrams for describing the counting pixel of FIG. 4.
Figure 8B:
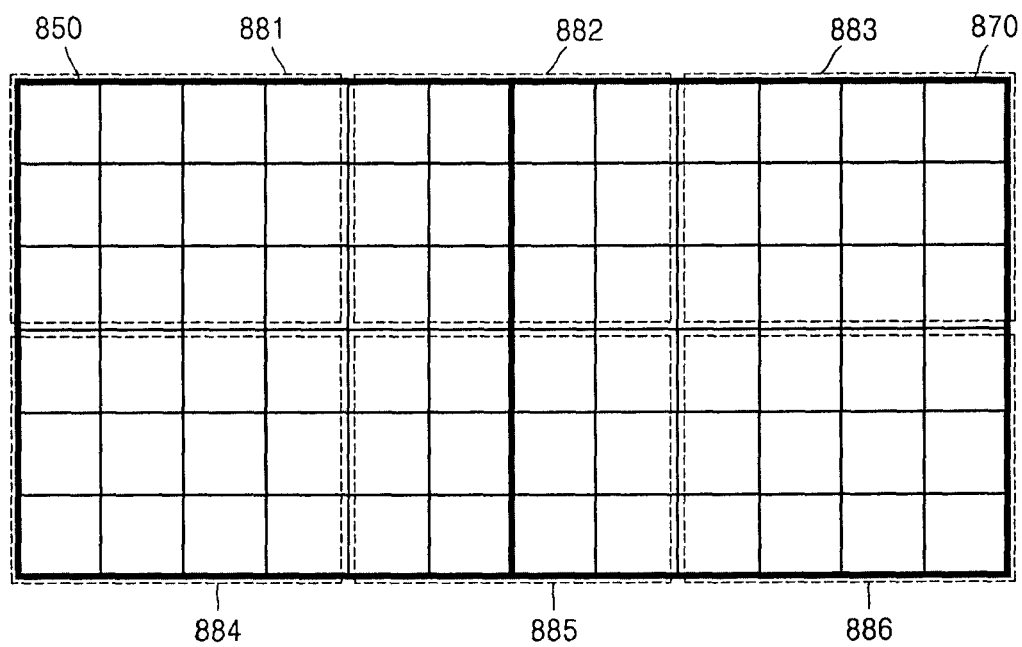

FIGS. 8A and 8B are diagrams for describing a counting pixel 411 of FIG. 4.

In the radiation detector 400, the number of photons counted by at least one of counting pixels may correspond to one image pixel value of a restored image. Specifically, at least one of counting pixels may be grouped, and the radiation detector 400 may generate one image pixel value of a CT image by using the number of photons counted by one group including the plurality of counting pixels. Herein, the grouped counting pixels refer to as counting pixel group. In detail, the total number of photons counted by one counting pixel group (for example, 821) may correspond to one image pixel value of a restored CT image. In the radiation detector 400, the number of photons counted by one counting pixel may also correspond to the one image pixel value of the restored image.

In FIG. 8A, a case in which one pixel 810 includes 24 counting pixels (6*4 pixels) is illustrated as an example. In FIG. 8B, a case in which two adjoining pixels 850 and 870 each include 36 counting pixels (6*6 pixels) is illustrated as an example.

Referring to FIG. 8A, one pixel 810 includes a plurality of counting pixels which are arranged adjacent to each other, and each of a plurality of counting pixel groups 821 to 826 includes a number of counting pixels. All counting pixels belong to one of the plurality of counting pixel groups 821 to 826, and all of the plurality of counting pixel groups 821 to 826 are within the boundary of one pixel 810. The total number of photons counted by the plurality of counting pixel groups 821, 822, 823, 824, 825 and 826 may correspond to one image pixel value of a restored image. In detail, the total number of photons counted by one counting pixel group (for example, 821) may correspond to one image pixel value of a restored CT image.

In FIG. 8A, a case in which one counting pixel group corresponding to one image pixel value includes four counting pixels is illustrated as an example. In this case, when one pixel 810 includes 24 counting pixels (6*4 pixels), the one pixel 810 may be divided into 6 counting pixel groups 821, 822, 823, 824, 825, and 826 (2*2 counting pixel groups), and the one pixel 810 may generate 6 image pixel values from a restored image. In detail, referring to FIG. 8A, one pixel 810 includes six counting pixel groups 821 to 826. Here, the counting pixel groups 821 to 826 may constitute an image pixel that generates one pixel value, and thus, the one pixel 810 includes six image pixels. Therefore, the number of counting pixel groups included in the radiation detector 400 may be equal to or more than the number of pixels included in the radiation detector 400. Also, a size of a counting pixel group (for example, 821) may be equal to or smaller than that of the pixel 810.

As an alternative example, 24 counting pixels included in one pixel 810 may be divided into four counting pixel groups of 3*2 counting pixels, and the one pixel 810 may generate a single combined count value as an image pixel value or 4 different image pixel values (one for each of the 4 counting pixel groups) for a restored image.

Referring to FIG. 8B, two adjacent pixels 850 and 870 are illustrated.

In the radiation detector 400, a plurality of counting pixels included in a plurality of pixels may be divided into a plurality of counting pixel groups, and the number of photons counted by one of the divided groups may correspond to one image pixel value of a restored image.

Referring to FIG. 8B, 72 counting pixels included in the two adjacent pixels 850 and 870 may be divided into 6 counting pixel groups 881, 882, 883, 884, 885, and 886. Specifically, one image pixel value of a restored image may be determined according to the total number of photons counted by the 12 counting pixels included in one counting pixel group (for example, 881). The counting pixel groups 881 to 886 cross boundaries between pixels 850, 870. Consequently, pixels may be redefined as smaller counting pixels groups than the total number of counting pixels in the original pixel 810, allowing also faster acquisition of desired count values of incident numbers of photons, to arrive quicker at measurement results that allow image restoration at a desired level of detail or resolution. The reason for this is that the area of these redefined pixels, which correspond with the counting pixel groups and which are smaller than the original pixel 810, is smaller than the original pixels, and consequently lower numbers of photons impinge in the same amount of time in these redefined pixels. Since the separately operating counting pixels allow an increase in the resolution of spatially distribution of impinging photons, and the counting pixel groups forming redefined pixels are smaller than the original pixel 810 size, a resulting level of detail or resolution may even be increased, as is described further below.

Moreover, referring to FIG. 8B, six counting pixel groups 881 to 886 are included in two pixels 850 and 870. That is, a size of a pixel (for example, 850) included in the radiation detector 400 may be equal to or larger than that of a counting pixel group (for example, 881).

Figure 9:
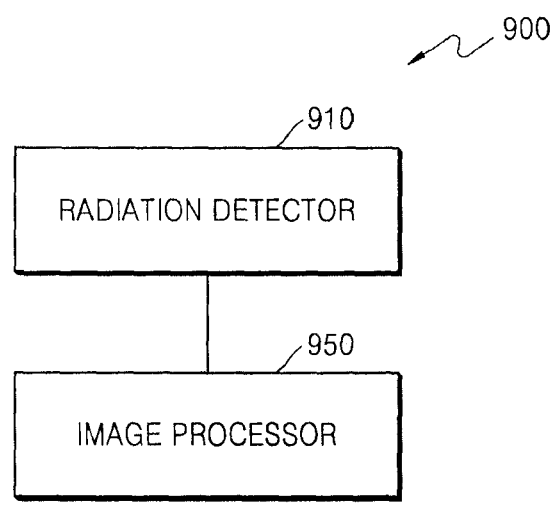
FIG. 9 is a diagram illustrating a computed tomography apparatus according to an embodiment of the present invention.

FIG. 9 is a diagram illustrating a computed tomography apparatus 900 according to an embodiment of the present invention.

The computed tomography apparatus 900 according to an embodiment of the present invention includes a radiation detector 910 and an image processor 950. The radiation detector 910 has the same technical spirit and configuration as those of the radiation detector according to an embodiment of the present invention described above with reference to FIGS. 1B and 4 to 8, and thus, the same descriptions provided above are not repeated.

Moreover, the image processor 950 may be an element corresponding to the image processing unit 196 described above with reference to FIG. 1B. Alternatively, the image processor 950 may be an element corresponding to the external medical apparatus 164 as in FIG. 2, which is connected to the CT system 20 over the wired/wireless network 15.

Referring to FIG. 9, the radiation detector 910 includes a plurality of pixels that detect radiation. Here, each of the plurality of pixels includes at least one of counting pixels. For, example, one pixel may include m counting pixels.

Each of the plurality of counting pixels includes the radiation absorption layer 412 that converts an incident X-ray photon into an electrical signal, the photon processor 413 that counts the number of photons converted into a plurality of electrical signals, and the memory (not shown) that stores the number of absorbed photons and has a storage capacity of an n/m value when a corresponding pixel absorbs n number of photons.

The image processor 950 reconstructs a CT image based on the number of photons detected by the radiation detector 910. For example, the image processor 950 may generate a CT image, an OCT image, a PET-CT image, or an X-ray image, based on the number of photons sensed by the radiation detector 910. Hereinafter, a case in which the image processor 950 restores a CT image has been described above as an example.

Specifically, the image processor 950 may generate one image pixel value of the CT image by using the number of photons counted by a counting pixel group. Here, the counting pixel group includes at least one counting pixel included in at least one pixel.

Moreover, the image processor 950 may generate one image pixel value of the CT image by using the number of photons counted by one counting pixel.

Moreover, a counting pixel group corresponding to one image pixel value in a restored CT image may include a plurality of counting pixels which are included in one pixel and are arranged adjacent to each other.

Moreover, the counting pixel group corresponding to the one image pixel value in the restored CT image may include a plurality of counting pixels which are included in a plurality of pixels and are arranged adjacent to each other.

For example, when each pixel includes 24 counting pixels, as illustrated in FIG. 8A, the image processor 950 may divide the 24 counting pixels included in one pixel into 6 groups, and generate one image pixel value from a restored CT image by using the number of photons counted by one of the 6 counting pixel groups. That is, in this case, photons detected by one pixel are used to generate 6 image pixel values from the restored CT image.

As another example, when each pixel includes 36 counting pixels, as illustrated in FIG. 8B, the image processor 950 may divide 72 counting pixels included in two pixels into 6 groups, and generate one image pixel value from a restored CT image by using the number of photons counted by one of the 6 counting pixel groups. That is, in this case, photons detected by counting pixels in two pixels are used to generate 6 image pixel values from the restored CT image.

The image processor 950 may adjust the number of counting pixels, used to generate one image pixel value from a restored CT image, according to a resolution of the restored CT image. For example, when desiring to generate a super high-resolution CT image, the image processor 950 may generate one image pixel value from the restored CT image by using the number of photons counted by one counting pixel. This may or may not have an effect on the parameters during the certain time, such as the tube voltage or the length of this time, or the like.

The radiation detector 910 may detect incident radiation for a certain time (an exposure Lime) to sample the detected radiation that is incident during the certain time. For example, the number of incident photons in a general diagnostic radiation detector may be about 500 M corresponding to an area of 1 mm*1 mm per second. Therefore, a related art radiation detector that performs a photon counting operation for each pixel measures energies of incident photons for a certain sampling time, and counts the number of photons having energy equal to or greater than a certain value. When 500 M photons are incident on an area of 1 mm*1 mm per second, the related art radiation detector samples one photon for 2 nsec (1/500 M sec). According to the Nyquist sampling theorem, the related art radiation detector reliably samples one photon per 1 nsec corresponding to one half of 2 nsec.

However, it is difficult to perform an operation, which measures and compares energies of photons to count the number of photons, within 1 nsec. Even when two photons impinge on entirely different location of a surface 640 of a pixel 600 in FIG. 6A, there is a risk that the count value may be incremented only by a number of 1, even though two photons will have impinged. Also, even though a circuit that measures and compares energies of photons to count the number of photons performs the above-described measurement and comparison operation for the sampling time, it is difficult to adjust a response of a radiation absorption layer absorbing radiation to the sampling time. Also, when a number of photons are simultaneously incident onto a comparator, an operation of comparing energies of photons may not normally be performed. Also, while a comparing and counting operation for energy of one photon is being performed, if another photon is incident, the counting operation may not normally be performed, and count value for the later impinging photon may be lost.

Moreover, a related art counting detector counts photons by pixel and includes a memory that stores the number of counted photons by frame, or the memory stores the number of photons counted by each group composed of a plurality of pixels.

As described above, in the radiation detector and the apparatus according to an embodiment of the present invention, each of the plurality of pixels included in the radiation detector includes a number of m counting pixels, each of which includes the photon processor that counts photons and the memory that stores the number of counted photons. Specifically, each of the plurality of counting pixels separately performs an operation of counting photons and an operation of storing the number of counted photons. When a corresponding pixel absorbs and counts n number of photons, the memory of a corresponding counting pixel has the storage capacity of an n/m value.

Therefore, in the radiation detector according to an embodiment of the present invention, since a photon counting operation is separately performed for each counting pixel, the number of photons to be processed for each counting pixel is reduced by n/m compared with the number of photons to be processed by the related art pixels. Accordingly, a sampling time of $1/(n/m)$ sec is available and secured for each photon, which alleviates requirements on the radiation absorption layer, the photon processor, the comparator and the memory—if separately provided. That is, in comparison with the related art radiation detector in which a sampling time for each photon is $1/n$ sec, the radiation detector according to an embodiment of the present invention secures the sampling time of $1/(n/m)$ sec corresponding to m times the sampling time of the related art radiation detector. Accordingly, a degree of accuracy in counting photons is enhanced, and the radiation absorption layer may sufficiently count the number of absorbed photons. Also, since the number of photons processed by the comparator and the counter is reduced by n/m, the radiation detector according to an embodiment of the present invention solves a problem that the related art radiation detector cannot normally count the number of photons when the photons are practically simultaneously incident, i.e. impinging within a time period in which according to the above discussed Nyquist sampling theorem the absorption layer, comparator and counter may not be able to distinguish between separately impinging photons.

Based on the foregoing description, it should be understood that pixels are referred to as the smallest building blocks for providing numbers of impinging photons and to generate therefrom reconstructed images. By dividing the contribution to counted numbers of impinging photons over a number m of counting pixels, more accurate and quicker accumulation of required numbers of photons can be achieved for pixels, for example to achieve a desired high count value in a certain or available time period, which to date has eluded the skilled persons in this technical field for a required count value of for example 200M photons per second. Moreover, embodiments of the present disclosure allow for recombination of selected numbers of counting pixels to even re-define pixels, and thus take varying circumstances with respect to for instance photon influx into account, and/or even lower the number of counting pixels per pixel to increase the acquisition time of a desired or required count value.

Moreover, the memory of each counting pixel is designed to have a storage capacity of an n/m value, and thus, a size of the memory included in each counting pixel is minimized. Therefore, according to the embodiments of the present invention, the radiation detector is realized by including one memory in each counting pixel.

Moreover, the radiation detector and the apparatus, such as a computed tomography apparatus, according to an embodiment of the present invention generate one image pixel value of a restored image by using the total number of photons counted by at least one counting pixel, thereby realizing a quality of an image according to an image resolution desired by a user.

The embodiments of the present invention may be written as computer programs and may be implemented in general-use digital computers that execute the programs using a computer-readable recording medium.

Examples of the computer-readable recording medium include magnetic storage media (e.g., ROM, floppy disks, hard disks, etc.), optical recording media (e.g., CD-ROMs or DVDs), etc.

It should be understood that the exemplary embodiments described therein should be considered in a descriptive detect only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the scope of the present invention as defined by the following claims.

What is claimed is:

1. A radiation detector comprising:
   a plurality of image pixels, wherein each image pixel of the plurality of image pixels includes a plurality of counting pixels,
   each counting pixel of the plurality of counting pixels comprising:
      a radiation absorption layer that converts incident photons, which are incident on a corresponding counting pixel of the plurality of counting pixels, into an electrical signal,
      a comparator that compares the electrical signal transferred from the radiation absorption layer included in the corresponding counting pixel with a reference value to determine whether the electrical signal exceeds the reference value, and outputs an output signal in response to the electrical signal exceeding the reference value, and
      a counting memory that corresponds to the corresponding counting pixel in a one to one relationship, counts a number of the incident photons, based on the output signal of the comparator, and stores the number of the counted incident photons,
   wherein a number of the plurality of image pixels is smaller than a number of the plurality of counting pixels included into the plurality of image pixels.

2. The radiation detector of claim 1, wherein the counting memory is configured to count the number of the incident photons based on the electrical signal, which is generated directly by the radiation absorption layer by converting the incident photons into an electric charge to detect the incident photons.

3. The radiation detector of claim 1, wherein the counting memory is configured to store a smaller number of the counted incident photons than a number of photons which are incident on a corresponding image pixel of the plurality of image pixels, for a certain time.

4. The radiation detector of claim 1, wherein each image pixel of the plurality of image pixels corresponds to a pixel of the radiation detector,
the plurality of counting pixels, which are included in the pixel, are two counting pixels of the plurality of counting pixels, the two counting pixels being arranged as a counting pixel group, and
a number of the incident photons counted by the counting pixel group corresponds to one image pixel value in an image.

5. The radiation detector of claim 1, wherein the radiation absorption layer comprises cadmium telluride (CdTe).

6. The radiation detector of claim 1, wherein each counting pixel of the plurality of counting pixels is a partial pixel included within a corresponding image pixel of the plurality of image pixels.

7. A tomography apparatus comprising:
the radiation detector of claim 1; and
an image processor coupled to the radiation detector and configured to generate an image,
wherein each image pixel of the plurality of image pixels corresponds to one pixel value in the image.

8. A tomography apparatus comprising:
the radiation detector of claim 1; and
an image processor coupled to the radiation detector and configured to generate an image,
wherein each image pixel of the plurality of image pixels is a pixel of the radiation detector, and
the number of the incident photons counted by the plurality of counting pixels, which are included in a corresponding image pixel of the plurality of image pixels, corresponds to one image pixel value in the image.

9. A tomography apparatus comprising:
the radiation detector of claim 1; and
an image processor coupled to the radiation detector and configured to generate an image,
wherein the plurality of counting pixels of the radiation detector are arranged as groups of counting pixels,
wherein each group of the groups of counting pixels comprises adjacent counting pixels, and
wherein a number of the incident photons counted by each group of the groups of counting pixels corresponds to one image pixel value in the image.

10. A radiation detector including:
a plurality of pixels, which sense radiation, each pixel of the plurality of pixels comprising a plurality of counting pixels,
each counting pixel of the plurality of counting pixels comprising:
a radiation absorption layer that converts incident photons, which are incident on a respective counting pixel of the plurality of counting pixels, into an electrical signal,
a comparator that compares the electrical signal transferred from the radiation absorption layer included in the respective counting pixel with a reference value to determine whether the electrical signal exceeds the reference value, and outputs an output signal in response to the electrical signal exceeding the reference value, and
a counting memory that corresponds to the respective counting pixel in a one to one relationship, counts a number of the incident photons, based on the output signal of the comparator, and stores the number of the counted incident photons.

11. The radiation detector of claim 10, wherein each counting pixel of the plurality of counting pixels is configured to count a smaller number of the incident photons than a number of photons incident on a corresponding pixel of the plurality of pixels.

12. The radiation detector of claim 10, wherein one of the plurality of pixels includes the plurality of counting pixels being arranged adjacent each other as a counting pixel group, and
a total number of the incident photons, counted by the counting pixel group, corresponds to one image pixel value in an image.

13. The radiation detector of claim 10,
wherein the radiation absorption layer of each counting pixel of the plurality of counting pixels is disposed at a surface of the radiation detector that faces an X-ray source,
wherein the radiation detector includes a semiconductor layer which is disposed underneath the radiation absorption layer, and
wherein each counting memory is embodied in the semiconductor layer, so that each counting memory individually corresponds to each counting pixel included into the radiation absorption layer.

14. A tomography apparatus comprising:
the radiation detector of claim 10; and
an image processor coupled to the radiation detector and configured to generate an image,
wherein the number of the incident photons counted by the counting memory corresponds to one image pixel value in the image.

15. A tomography apparatus comprising:
the radiation detector of claim 10; and
an image processor coupled to the radiation detector and configured to generate an image,
wherein the plurality of counting pixels of the radiation detector are arranged as groups of counting pixels,
wherein each group of the groups of counting pixels comprises adjacent counting pixels, and
wherein a number of the incident photons counted by each group of the groups of counting pixels corresponds to one pixel value in the image.

16. A tomography imaging apparatus comprising:
a radiation detector that includes a plurality of image pixels, each image pixel of the plurality of image pixels including a plurality of counting pixels; and
an image processor that reconstructs a tomography image, based on a number of photons sensed by the radiation detector,
wherein a number of the plurality of image pixels is smaller than a number of the plurality of counting pixels included into the plurality of image pixels, and
wherein each counting pixel of the plurality of counting pixels comprises:
a radiation absorption layer that converts incident photons, which are incident on a corresponding counting pixel of the plurality of counting pixels, into an electrical signal,
a comparator that compares the electrical signal transferred from the radiation absorption layer included in the corresponding counting pixel with a reference value to determine whether the electrical signal exceeds the reference value, and outputs an output signal in response to the electrical signal exceeding the reference value, and a counting memory that corresponds to the corresponding counting pixel of the plurality of counting pixels in a one to one relationship, counts a number of the incident photons, based on the output signal of the comparator, and stores the number of the counted incident photons.

* * * * *